(12) United States Patent
Moon

(10) Patent No.: US 7,521,232 B2
(45) Date of Patent: Apr. 21, 2009

(54) EMISSIVE SPECIES FOR CLINICAL IMAGING

(75) Inventor: Joongho Moon, Natick, MA (US)

(73) Assignee: ICx Nomadics, Inc., Stillwater, OK (US)

(*) Notice: Subject to any disclaimer, the term of this patent is extended or adjusted under 35 U.S.C. 154(b) by 0 days.

(21) Appl. No.: 11/444,142

(22) Filed: May 31, 2006

(65) Prior Publication Data

US 2007/0281289 A1 Dec. 6, 2007

(51) Int. Cl.
*C12N 5/00* (2006.01)
(52) U.S. Cl. ...................................... 435/325
(58) Field of Classification Search ........................ None
See application file for complete search history.

(56) References Cited

U.S. PATENT DOCUMENTS

| 6,605,693 B1 | 8/2003 | Becker et al. |
| 6,743,640 B2 | 6/2004 | Whitten et al. |
| 2005/0220714 A1 | 10/2005 | Kauzlarich et al. |

FOREIGN PATENT DOCUMENTS

WO WO 2007/006773 A2 6/2007

OTHER PUBLICATIONS

Lim et al. Pharmaceutical Research 2004 21(11):1985-1992.*
Funhoff et al. Journal of Controlled Release Jan. 2005, 101:233-246.*
Wosnick et al. Synthesis and application of poly(phenylene ethynylene)s for bioconjugation: a conjugated polymer-based fluorogenic probe for proteases, J. Am. Chem. Soc. 2005, 127:3400-3405.*
Lee et al. "Proteolytically Degradable Hydrogels with a Fluorogenic Substrate for Studies of Cellular Proteolytic Activity and Migration", Biotechnol. Prog. 2005, 21:1736-1741.*
Disney, Matthew D. et al., "Detection of Bacteria with Carbohydrate-Functionalized Fluorescent Polymers," *J. Am. Chem. Soc.* 2004, 126, 13343-13346.
Jensen, Keith D. et al., "Cytoplasmic Delivery and Nuclear Targeting of Synthetic Macromolecules," *Journal of Controlled Release* 2003, 87, 89-105.
Kim, I. et al., "Nonspecific Interactions of a Carboxylate-Substituted PPE with Proteins. A Cautionary Tale for Biosensor Applications," *Langmuir* 2005, 21, 7985-7989.
Li, Z.F. et al., "Water-Soluble Poly(acrylic acid) Grafted Luminescent Silicon Nanoparticles and Their Use as Fluorescent Biological Staining Labels," *Nano Lett.* 2004, 4(8), 1463-1467.
Orynbayeva, Z. et al., "Visualization of Membrane Processes in Living Cells by Surface-Attached Chromatic Polymer Patches," *Angew. Chem. Int. Ed.* 2005, 44, 1092-1096.
Wu, Zhaoqiang et al., "Novel Water-Soluble Fluorescent Polymer Containing Recognition Units: Synthesis and Interactions with PC12 Cell," *European Polymer Journal* 2005, 41, 1985-1992.
Yamaguchi, Y. et al., "Light-Emitting Efficiency Tuning of Rod-Shaped π-Conjugated Systems by Donor and Acceptor Groups," *J. Am. Chem. Soc.* 2005, 127, 9332-9333.
Moon, J.H., et al., "Live-Cell Permeable Poly(*p*-phenylene ethynylene)," *Angew. Chem. Int. Ed.*, 2007, 46, 8223-8225.

* cited by examiner

*Primary Examiner*—Jon P Weber
*Assistant Examiner*—Bin Shen
(74) *Attorney, Agent, or Firm*—Wolf, Greenfield & Sacks, P.C.

(57) ABSTRACT

The present invention relates to materials and methods useful in the study of cells and species associated with cells. Materials of the present invention may include emissive, photostable organic molecules (e.g., conjugated polymers, conjugated oligomers) that are appropriately functionalized to interact with a cell with essentially no disruption in normal cell functioning. The present invention may be useful in, for example, cell imaging, cell tracking, in vivo monitoring of cellular events, drug delivery, and determination of biological species. In one embodiment, a conjugated polymer or oligomer may be internalized into a cell and may exhibit a strong and stable emissive signal, allowing the cell to be monitored under extensive microscopic conditions for extended periods of time.

21 Claims, 14 Drawing Sheets a.)

b.)

c.)

n=0,1,2,3,...    X = halide

Y = NH$_2$, OH, CO$_2$H, NH(CH$_2$CO$_2$H)$_2$, C(CH$_3$)(CO$_2$H)$_2$, C(CH$_3$)(CO$_2$Et)$_2$, C(CO$_2$H)$_3$, N(CH$_3$)$_3$X, N(CH$_3$)$_3$OTs, NHCO$_2$C(CH$_3$)$_3$, a.)

b.)

SEQUENCE LISTING

<160> NUMBER OF SEQ ID NOS: 3

<210> SEQ ID NO 1
<211> LENGTH: 17
<212> TYPE: PRT
<213> ORGANISM: artificial sequence

```
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Acetyl group attached
<220> FEATURE:
<221> NAME/KEY: MISC_FEATURE
<222> LOCATION: (1)..(1)
<223> OTHER INFORMATION: N-(2-(3-(thio)-2,5-dioxopyrrolidin-1-
      yl)ethyl)acetamide functionalized polymer attached

<400> SEQUENCE: 1

Cys Val Lys Arg Lys Lys Lys Pro Pro Val Lys Arg Lys Lys Lys Pro
1               5                   10                  15

Pro

<210> SEQ ID NO 2
<211> LENGTH: 16
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetamide functionalized polymer attached
<220> FEATURE:
<221> NAME/KEY: MISC_FEATURE
<222> LOCATION: (2)..(2)
<223> OTHER INFORMATION: Lys includes Boc group
<220> FEATURE:
<221> NAME/KEY: MISC_FEATURE
<222> LOCATION: (3)..(3)
<223> OTHER INFORMATION: Arg includes Pbf group
<220> FEATURE:
<221> NAME/KEY: MISC_FEATURE
<222> LOCATION: (4)..(6)
<223> OTHER INFORMATION: Lys includes Boc group
<220> FEATURE:
<221> NAME/KEY: MISC_FEATURE
<222> LOCATION: (10)..(10)
<223> OTHER INFORMATION: Lys includes Boc group
<220> FEATURE:
<221> NAME/KEY: MISC_FEATURE
<222> LOCATION: (11)..(11)
<223> OTHER INFORMATION: Arg includes Pbf group
<220> FEATURE:
<221> NAME/KEY: MISC_FEATURE
<222> LOCATION: (12)..(14)
<223> OTHER INFORMATION: Lys includes Boc group
<220> FEATURE:
<221> NAME/KEY: MISC_FEATURE
<222> LOCATION: (16)..(16)
<223> OTHER INFORMATION: benzyloxy functionalized resin attached

<400> SEQUENCE: 2

Val Lys Arg Lys Lys Lys Pro Pro Val Lys Arg Lys Lys Lys Pro Pro
1               5                   10                  15

<210> SEQ ID NO 3
<211> LENGTH: 16
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetamide functionalized polymer attached
```

```
<400> SEQUENCE: 3

Val Lys Arg Lys Lys Lys Pro Pro Val Lys Arg Lys Lys Lys Pro Pro
1               5                   10                  15
```

EMISSIVE SPECIES FOR CLINICAL IMAGING

STATEMENT REGARDING FEDERALLY SPONSORED RESEARCH OR DEVELOPMENT

This invention was made with the support under the following government contract: DMI-0239285, awarded by the National Science Foundation. The government has certain rights in the invention.

FIELD OF THE INVENTION

The present invention relates to materials and methods useful in the study of biological systems, such as cells and species associated with cells.

BACKGROUND OF THE INVENTION

The study of signaling pathways in biological cells may lead to greater understanding of cellular responses to various disease-causing agents, resulting in improved treatment alternatives in the form of drugs that target specific pathways. Fluorescence-based biological assays have demonstrated tremendous value in allowing researchers to understand complex biological processes. For example, organic fluorescent molecules or green fluorescent proteins (GFPs) are commonly used materials for fluorescent tagging of biological substances, including cells, and have been utilized in cell imaging, cell tracking, and in vivo monitoring of cellular events. GFPs have excellent biological compatibility because they are genetically encoded and expressed by the cell itself. However, the poor photostability of some organic fluorophores and GFPs may cause difficulties in long-term monitoring of cellular events, where high sensitivity and high image resolution are often desired. Additionally, GFPs require a time-consuming process for establishing stable-expressing clones, which may limit their use in long-term imaging of live cells.

Fluorescent quantum dots (QDs) are nanometer-sized heavy metal or semiconductor particles that can be covalently linked to bio-recognition molecules such as peptides, antibodies, nucleic acids, or small-molecule ligands for application as fluorescent probes. QDs have high absorption coefficients, high photobleaching thresholds, and high quantum yields. However, despite the advantageous photophysical nature of QDs, they are also very highly toxic. To reduce the inherent toxicity of heavy metals, various chemical approaches have been applied, including coordination of small molecules, silylation, and encapsulation of lipids. Cell survivability in particular cell lines has been reported by decorations or biomolecule encapsulation of QDs; however, their toxicity still remains a problem. Initial investigation into CdSe QD toxicity using primary hepatocytes rich in metallothionein as a model for the liver clearly displayed that, under certain conditions, the QDs were cytotoxic. The toxicity was attributed to liberation of $Cd^{2+}$ ions during oxidation. Also, the surface modification of QDs resulted in decreased emission efficiency and poor colloidal stability. Another side effect of the surface coatings of QDs may be that the coatings can change dramatically with the movement, retention, and distribution of QDs. Also, size may often be the basic determinant for the photophysical properties of quantum dots, wherein a larger QD may have superior optical properties relative to a smaller QD.

Accordingly, improved methods are needed.

SUMMARY OF THE INVENTION

The present invention relates to compositions comprising a conjugated polymer or a conjugated oligomer, wherein the polymer or oligomer is capable of being inserted into a cell or a portion of the cell.

The present invention also provides methods for imaging a cell, comprising exposing a cell to an emissive, conjugated polymer or an emissive, conjugated oligomer, and imaging the cell via emission of the polymer or oligomer.

The present invention also provides methods for determining a cell, comprising exposing an emissive, conjugated polymer comprising a biological recognition entity or an emissive, conjugated oligomer comprising a biological recognition entity to an environment suspected of containing a cell, wherein the cell, if present, interacts with the biological recognition entity, and determining the cell via determination of emission of the polymer or oligomer.

The present invention also provides methods for determining a species associated with a cell, which interacts with a fluorophore, comprising exposing a cell to a conjugated polymer or a conjugated oligomer and a fluorophore, wherein the polymer or the oligomer is a fluorescence resonance energy transfer donor and the fluorophore is a fluorescence resonance energy transfer acceptor, exposing the polymer or the oligomer to a source of energy to form an excitation energy, allowing the excitation energy to transfer to the fluorophore, causing an emission from the fluorophore; and determining the species via determination of the emission.

The present invention also provides methods for delivering a biological agent, comprising introducing a conjugated polymer bound to a biological agent or conjugated oligomer bound to a biological agent into a cell.

Additionally, the present invention provides articles comprising a cell comprising an emissive, conjugated polymer or an emissive, conjugated oligomer, wherein the polymer or oligomer is inside the cell.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

DETAILED DESCRIPTION

Figure 1:
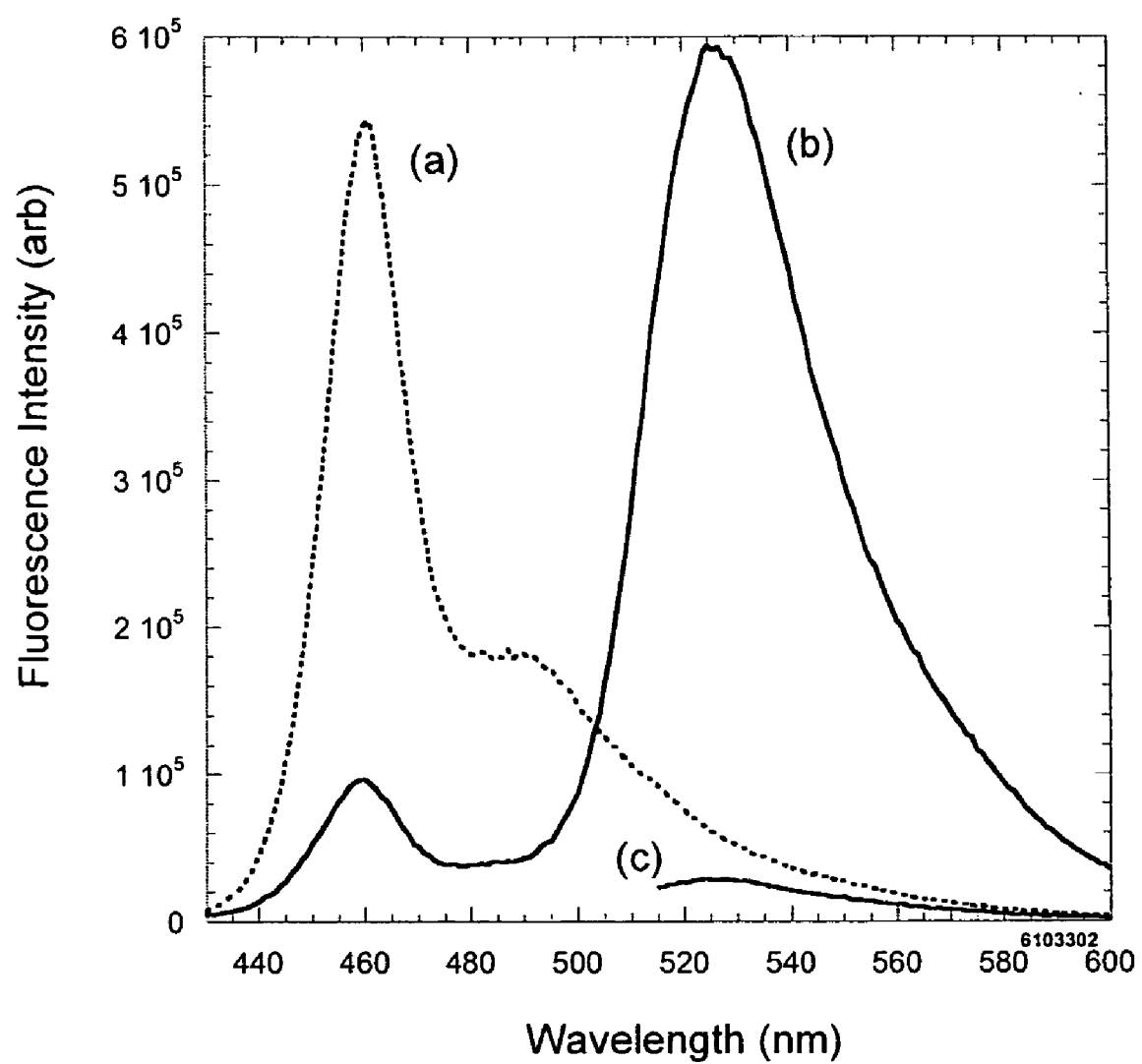
FIG. 1 shows the emission spectra of a (a) conjugated polymer (ex 420 nm), (b) acridine orange mixed with the conjugated polymer in a buffer (SSPE) (ex 420 nm), and (c) acridine orange with direct excitation at 490 nm.

The present invention relates to materials and methods useful in the study of cells and species associated with cells. Materials of the present invention may include organic molecules (e.g., conjugated polymers, conjugated oligomers) that are highly emissive and appropriately functionalized such that they may interact with a cell with essentially no disruption in normal cell functioning. The present invention may be useful in, for example, cell imaging, cell trafficking, in vivo monitoring of cellular events, drug delivery, determination of biological species, etc. For example, in one embodiment, a conjugated polymer or oligomer may be internalized into a cell and may exhibit a strong and stable emissive (e.g., fluorescent) signal, allowing the cell to be monitored under extensive microscopic conditions for extended periods of time. In some embodiments, the emissive, conjugated polymers or oligomers may be bound to a biological entity. Some advantages of the present invention include materials which have high photostability and low toxicity. Also, materials of the present invention are modular, and can be tailored to suit a wide variety of applications with relative ease.

The use of conjugated polymers and/or conjugated oligomers as emissive species and/or delivery agents or the like in connection with cells and related species provides significant advantage in that the materials are not only highly emissive and photostable, providing more reliable results and allowing for long-term monitoring of cellular events, but are also substantially non-toxic, employing biocompatible, organic materials without the use of heavy metals. It is believed that uses of such polymers and oligomers as described and claimed herein have not been realized in the prior art perhaps due to the inability of some or many conjugated polymers and oligomers to penetrate the cell membrane and/or allow for cell imagining, and/or the lack of recognition that this use could be possible. Prior unsuitable conjugated polymers or oligomers may have been unsuitable due to a lack of functionalization permitting penetration of the cell membrane. Additionally, some known conjugated polymers and oligomers may have been incompatible due to their large sizes and insolubility in aqueous, cell-compatible media.

In one embodiment, the present invention provides conjugated polymers and oligomers for use in the imaging, monitoring, and treatment of cells and species associated with cells. The conjugated materials may be appropriately functionalized such that they are soluble in aqueous solutions (e.g., neat water) and/or are able to traverse the cell membrane. Also, the conjugated materials may have reduced toxicity and may be capable of interacting with cells without damaging the cell or causing cell death. For example, materials of the invention may be capable of penetrating the cell membrane and/or the interior of the cell. In one embodiment, the conjugated material may be inserted into (i.e., may penetrate) the cell membrane. In one embodiment, the conjugated material may be inserted into portions of the cell interior, such as the cytoplasm or the nucleus.

Described in greater detail below are techniques for appropriate functionalization of conjugated materials of the invention, and/or selection of appropriate conjugated materials so that they can be used in connection with techniques described herein. Those of ordinary skill in the art, in connection with the direction provided herein and available knowledge in the art, will be able to appropriately select and/or construct suitable conjugated materials for techniques described herein.

As used herein, the term "polymer" is given its ordinary meaning in the art. Polymers are generally extended molecular structures comprising backbones which optionally contain pendant side groups. As used herein, "backbone" is given its ordinary meaning as used in the art, e.g., a linear chain of atoms within the polymer molecule by which other chains may be regarded as being pendant. Typically, but not always, the backbone is the longest chain of atoms within the polymer. A "conjugated" polymer is a polymer in which at least a portion of the polymer is conjugated, i.e. the polymer has at least one conjugated portion. "Conjugated," as used herein, refers to an interconnected chain of at least three atoms, each atom participating in delocalized bonding, such as pi-bonding or sigma-bonding. Electron density or electronic charge can be conducted along the conjugated portion of the polymer. For example, in pi-bonding, each p-orbital participating in conjugation may have sufficient overlap with adjacent conjugated p-orbitals. In another embodiment, a substantial length of the backbone (e.g., the entire backbone) may be conjugated. As used herein, an "oligomer" may refer to a polymer as described herein having 2-20 monomeric units. For example, an oligomer may refer to a dimer, a trimer, a tetramer, and the like.

In some embodiments, exposure of the polymer or the oligomer to a source of energy may cause an emission (e.g., fluorescence, phosphorescence, or chemiluminescence). The source of energy may comprise electromagnetic radiation, electrical energy, sound energy, thermal energy, or chemical energy. In a particular embodiment, exposure of the conjugated polymer or oligomer to electromagnetic radiation causes a fluorescence emission.

Examples of conjugated polymers or oligomers that can be used in the invention include polyacetylenes, polyarylenes such as polyphenylenes, polythiophenes, polypyrroles, poly (arylene vinylene)s such as poly(phenylenevinylene)s, poly (aryleneethynylene)s such as poly(phenylene-ethynylene)s, ladder polymers, oligomers thereof, combinations thereof, and the like. As used herein, a "ladder polymer" is a polymer having a backbone that cannot be severed without breaking at least two bonds. Co-polymers of these and/or other polymers are also polymers that can be used in the invention, for example, block, alternating, or random co-polymers, etc.

Embodiments of the invention may include conjugated polymers or oligomers, wherein the polymer or oligomer is capable of being inserted into (i.e., may penetrate) a cell or a portion of the cell. In some embodiments, the conjugated polymers or oligomers are poly(phenyleneethynylene)s, poly (paraphenylene)s, polythiophene, polyaniline, oligomers thereof, substituted derivatives thereof, combinations thereof, and/or the like. In one embodiment, the polymer or oligomer is a substituted poly(phenyleneethynylene). Conjugated polymers and oligomers of the invention may have any molecular weight to suit a particular application. For example, conjugated polymers of the invention may have a molecular weight greater than 10,000 Da. In certain embodiments, the conjugated polymer may have a molecular weight in the range from about 20,000 Da to 60,000 Da, or from about 30,000 Da to 50,000 Da, wherein the polymer is capable of being inserted into a cell or a portion of a cell. In some embodiments, the conjugated oligomers may have a molecular weight of less than 10,000 Da, less than 5,000 Da, or less than 1,000 Da, wherein the oligomer is capable of being inserted into a cell or a portion of the cell.

Conjugated materials may be critically functionalized to be biocompatible such that the material may interact with the cell without damaging the cell. For example, conjugated materials of the invention may comprise functional groups which render the materials water-soluble. In some cases, the conjugated materials may comprise functional groups which may facilitate penetration of the cell membrane. Examples of functional groups which may facilitate biocompatibility may be amine groups, charged functional groups such as ammonium, carboxylate, etc., or other hydrophilic groups.

In another embodiment, conjugated polymers and oligomers of the invention may comprise and/or be immobilized or fastened to a biological recognition entity. The biological recognition entity may be capable of specifically interacting with a cell or species associated a cell. For example, the biological recognition entity may specifically associate with the cell membrane, bypassing other biological species at the surface of the cell. In some cases, the biological recognition entity may also target the nuclear membrane barrier. In one embodiment, the biological recognition entity may be capable of having a specific binding interaction with a target species in a cell. As used herein, "binding" can involve any hydrophobic, non-specific, or specific interaction, and the term "biological binding" refers to the interaction between a corresponding pair of molecules that exhibit mutual affinity or binding capacity, typically specific or non-specific binding or interaction. Biological binding defines a type of interaction that occurs between pairs of molecules including proteins, nucleic acids, glycoproteins, carbohydrates, hormones, and the like. Specific examples include protein/carbohydrate, antibody/antigen, antibody/hapten, biotin/streptavidin, biotin/avidin, enzyme/substrate, enzyme/inhibitor, enzyme/cofactor, protein/substrate, protein/ligand, lectin/carbohydrate, receptor/hormone, receptor/effector, complementary strands of nucleic acid (e.g., DNA and/or RNA), protein/nucleic acid, repressor/inducer, ligand/receptor, virus/ligand, etc. "Specific interaction" is given its ordinary meaning as used in the art, i.e., an interaction between pairs of molecules where the molecules have a higher recognition or affinity for each other than for other, dissimilar molecules.

In one embodiment, the biological recognition entity is a peptide (e.g., a cell-penetrating peptide, signal peptides targeting the nuclear membrane). In one embodiment, the biological recognition entity is a protein. In one embodiment, the biological recognition entity is a nucleic acid (e.g., DNA, RNA, an oligonucleotide). In one embodiment, the biological recognition entity is a small interfering RNA (siRNA). Other examples of suitable biological recognition entities include folic acid, carbohydrates, antibodies, and the like.

In some embodiments, the present invention provides a method for imaging a cell involving exposing a cell to an emissive, conjugated polymer or an emissive, conjugated oligomer and imaging the cell via the emission of the polymer or oligomer. The conjugated materials of the invention may be internalized into cells to interact with the cell and species associated with the cell. In some embodiments, the conjugated polymer or oligomer interacts with a specific target species in the cell. Methods of the present invention may be used to study processes involving real-time imaging of the structure, function, properties, and metabolism of cells, and other cellular processes including the biophysics of molecular assemblies, membranes, organelles, and macromolecules. For example, a conjugated polymer may specifically interact with the receptor ligand of a protein, allowing single protein movement in live cells to be monitored by monitoring the emission of the conjugated polymer. In one embodiment, a conjugated polymer or oligomer may be internalized into a specific portion of the cell (e.g., nucleus, nuclear membrane, cytoplasm, cell membrane, etc.). The ability to study the signaling pathways in cells may facilitate diagnosis, drug delivery, and disease prevention.

In one aspect, the present invention provides methods for the determination of cells and/or species associated with cells without disturbing the normal function of the cell. That is, methods of the invention comprise the use of conjugated polymers or oligomers whose size may be sufficiently small as to not, for example, disrupt the structure of the cell membrane, or other structures within the cell. In other embodiments, conjugated polymers or oligomers may be functionalized such that they are inert to (e.g., do not chemically or physically react with) species within the cell to interrupt cellular processes or to cause cell death. The determination of such biomolecules may be a critical factor in studying complex and dynamic cellular events in living organisms. In one embodiment, methods of the invention may be used to determine specific types of cells or biomolecules associated with cells, such as nucleic acids, oligonucleotides, proteins, pathogens, metabolites, and the like. In one embodiment, an emissive, conjugated polymer or oligomer of the invention may comprise a biological recognition entity that specifically interacts with, for example, a cancer cell. The presence, location, and/or amount of the cancer cells may be determined, for example, by observing the emission of the conjugated polymer or oligomer associated with the cells or species within the cells. In another embodiment, an emissive, conjugated polymer or oligomer of the invention may comprise a DNA strand that specifically interacts with a species having the complementary DNA strand to produce an emission which determines the species. As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

Conjugated polymer and oligomers of the invention may also be used in combination with an additional fluorophore, such as a small organic molecule, a fluorescent dye, green fluorescent protein, or the like, to enhance the performance of the fluorophore in cell imaging, cell monitoring, cell determination, etc. Such fluorophores may be unstable and may often undergo photobleaching, making the quantitative (and long-term) study of biological systems difficult. Conjugated polymers and oligomers of the present invention may be useful in enhancing the photostability of fluorophore by, for example, undergoing fluorescence resonance energy transfer (FRET) with a fluorophore. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species.

In one embodiment, the present invention provides a method for determining a species associated with a cell, wherein the species interacts with a fluorophore. The cell may be exposed to a conjugated polymer or a conjugated oligomer and a fluorophore, wherein the polymer or the oligomer is a FRET donor and the fluorophore (e.g., small organic molecule, fluorescent dye, GFP) is a FRET acceptor. Exposure of the conjugated polymer or oligomer to a source of energy may form an excitation energy, which may then be transferred to the fluorophore, causing an emission from the fluorophore. The species may be determined (e.g., observed, quantified, etc.) by the emission. Such methods may allow for reduced photobleaching in fluorophores and, in some cases, amplification of emission, allowing for more reliable quantification of fluorescence emission.

In an illustrative embodiment, a conjugated polymer of the invention may be combined in solution with acridine orange to exhibit a 100-fold enhancement in emission of the acridine orange via FRET from the conjugated polymer. FIG. 1A shows the fluorescence emission spectrum of a conjugated polymer with an emission of about 460 nm, and FIG. 1B shows the fluorescence emission spectrum of the same conjugated polymer combined with acridine orange (in a SSPE buffer) upon excitation at 420 nm. As shown in FIG. 1B, the emission at 460 nm is substantially decreased, and the majority of the emission occurs at about 530 nm. This indicates that, in the presence of acridine orange, energy transfer occurs efficiently between the conjugated polymer and acridine orange such that substantially all observed emission occurs at the emission wavelength of acridine orange. The emission of the conjugated polymer and acridine orange shows a strong FRET enhancement (e.g., 100-fold) in the emission of the fluorescent dye when compared with the emission of acridine orange with direct excitation at 490 nm (FIG. 1C).

In some embodiments, the present invention may be useful in delivering a biological agent to a cell. As used herein, a "biological agent" may be an agent that may be administered to a human or animal body for any purpose, including therapeutic, pharmaceutical, pharmacological, diagnostic, cosmetic and prophylactic agents. The term "biological agent" may also be used to include any agents which may administered to plants by controlled release, such as agrochemicals including herbicides, pesticides and fertilizers. In some embodiments, the biological agent is a polypeptide, peptide or protein, a carbohydrate, or an oligonucleotide (e.g., DNA, RNA, siRNA, etc.). Examples of suitable biological agents include growth hormone, insulin, interferons (alpha, beta, gamma), erythropoietin, colony stimulating factors, parathyroid hormone, leutenizing hormone releasing hormone, calcitonin, heparin, somatostatin and various analogs thereof. The biological agent may also be an antigen for use in vaccines and these include polypeptides, proteins, glycoproteins that are obtained from bacterial, viral and parasitic sources or produced by synthetic methods. The term "antigen" is used herein to include any material which will cause an antibody reaction of any sort when administered.

In one embodiment, the conjugated polymer or oligomer may be bound to a biological agent and may interact with a cell to deliver the biological agent to the cell. As used herein, the term "bound to a biological agent" may refer to having any type of bond (e.g., covalent bonds, ionic bonds, hydrogen bonds, dative bonds, or the like) or association with a biological agent. In one embodiment, the conjugated polymer bound to a biological agent or conjugated oligomer bound to a biological agent may deliver a biological agent to a cell while substantially simultaneously being monitored using the light emission from the polymer or the oligomer. In this arrangement, the conjugated polymer or oligomer may function as both a delivery vehicle and an emissive species, eliminating the need for an additional fluorophore to monitor the delivery of the biological agent. In some embodiments, the light emission of the conjugated polymer or oligomer may indicate delivery of the biological agent into the cell. In some cases, methods of the present invention allow the biological agent to be monitored for a relatively longer period of time due to the photostability of the conjugated polymers or oligomers. As such, the effects of long term exposure to the biological agent may be monitored.

The present invention may be applied to any type of biological cell. Examples include epithelial cell lines (e.g., Chinese hamster ovary, CHO-K1, ATCC CCL-61) and fibroblast cell lines (e.g., embryonic mouse, NIH/3T3, ATCC CRL-1658), which are both known to be effective in liposome-mediated transfer of nucleic acids. The permeability, distribution, nonspecific binding, specificity, and toxicity of conjugated materials of the invention may be examined for a particular type of cell line. In one embodiment, permeability screening of conjugated polymers or oligomers may provide information regarding the mechanism of cellular uptake (e.g., endocytosis). Upon determination of their presence in the cell (e.g., in or on the cell membrane, the cytoplasm, or the nucleus), the distribution, aggregation, retention, nonspecific interaction, and sensitivity of the conjugated materials may be determined.

In one embodiment, conjugated polymers and oligomers of the present invention may be used to interact with a cell or portions of a cell. For example, conjugated materials of the present invention may permeate the cell membrane partially, or, in some cases, may become fully internalized within the cell. In one embodiment, the conjugated polymer or oligomer may enter the cytoplasm.

In one embodiment, polymer and oligomers of the present invention may be used to enter the nucleus of a cell. That is, the conjugated polymer or oligomer may penetrate through the double-membrane nuclear envelope (e.g., nuclear pore complex) separating the cytoplasm from the cell nucleus. The nucleus may be a desired target in research of cellular monitoring since genomic DNA in the nucleus carries the genetic information of the cell. In addition, numerous nuclear proteins may be involved in critical cellular processes, such as DNA replication, recombination, RNA transcription, DNA damage and repair, genomic alternations, and cell cycle control. Methods of the invention may be useful in studying multiple pathways of nucleocytoplasmic transport that involve specific targeting sequences, such as nuclear localization sequences and cytosolic receptor molecules of the importin/karyopherin superfamily.

The specificity and permeability of the conjugated polymers and oligomers for a particular cell or species associated with a cell may be optimized by varying the size, functionality, and concentration of the polymer or oligomer, as further described herein. For example, functional groups which may increase the amphiphilic (e.g., lipophilic) nature of the conjugated polymer or oligomer may be used to increase compatibility with and affinity for the cell membrane, as well as the solubility of the conjugated polymer or oligomer in aqueous media (e.g., cell-culture media). Examples of suitable functional groups include neutral hydrophilic groups, such as amines, hydroxyls, and the like, and charged hydrophilic groups, such as anionic groups or cationic groups. Anionic groups may include, for example, carboxylates, sulfonates, phosphates, or the like, while cationic groups may include, for example, charged amines and charged heterocycles. Additionally, conjugated polymers and oligomers may be functionalized with cell-penetrating peptides in order to increase affinity for the cell membrane. Furthermore, the size of the conjugated polymers and oligomers may be selected based upon a particular application. For example, smaller conjugated polymers and oligomers may be used to enter the nucleus of a cell, while larger conjugated polymers and oligomers may be used to enter the cell membrane and/or the cytoplasm.

Alternate strategies may also be considered to optimize cell specificity and permeability, such as the use of nonadherent, dissociated cells, nonadherent carcinoma, or lymphocyte lines. In addition, liposome-mediated delivery of the conjugated polymer or oligomer may be considered.

Figure 2:
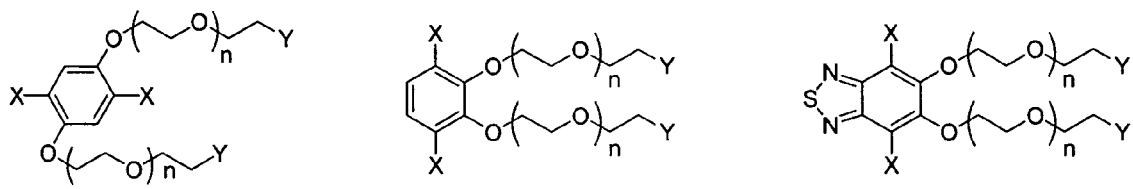
FIG. 2 shows examples of monomers that may be used in some embodiments of the present invention, including (a) dihaloaryl monomers, (b) diacetylene monomers, and (c) end capping monomers.
Figure 2:
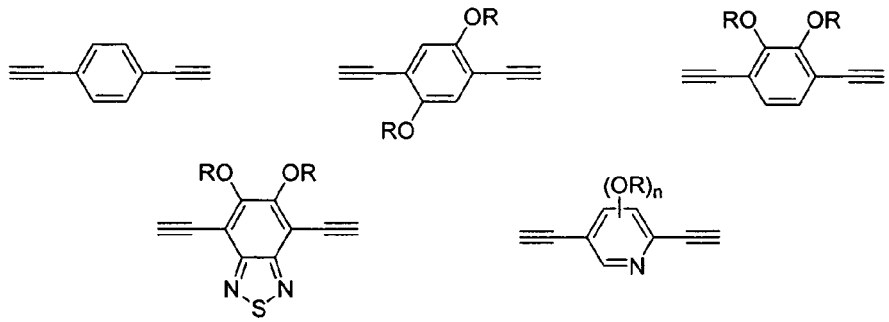
Figure 2:
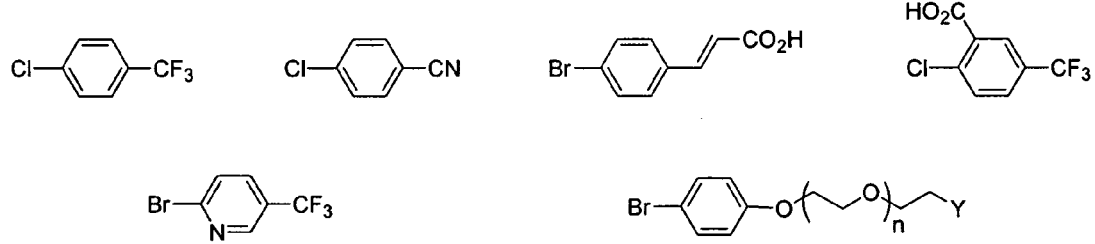
Figure 2:
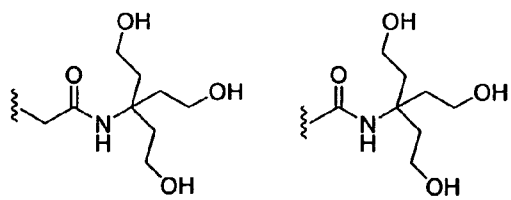
Figure 7:
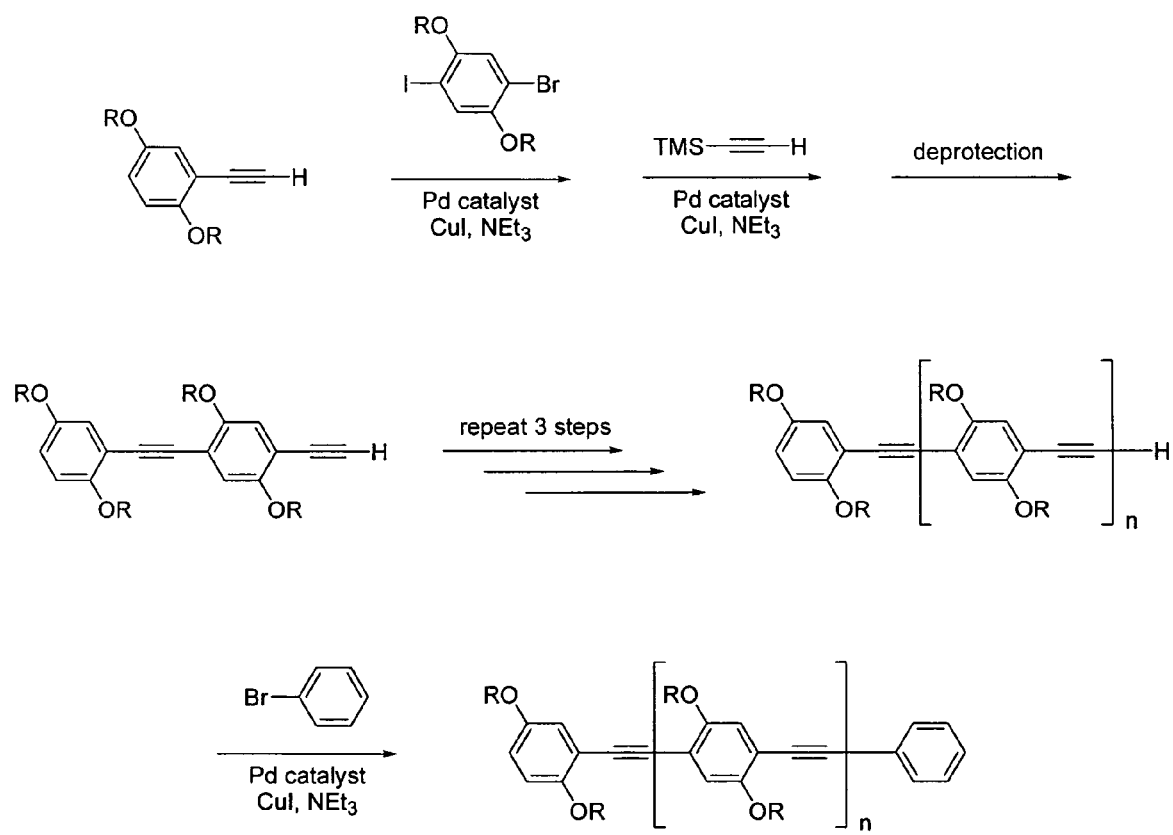
FIG. 7 shows the stepwise synthesis of a conjugated oligomer according to one embodiment of the invention.

Conjugated polymers and oligomers of the present invention may be synthesized by methods known in the art. For example, poly(phenyleneethynylene)s may be synthesized by palladium-catalyzed cross coupling between dihaloaryl monomers and diacetylene monomers. FIG. 2A shows some embodiments of suitable dihaloaryl monomers while FIG. 2B shows some embodiments of diacetylene monomers that may be used in the synthesis of materials of the present invention. End-capping monomers may also be utilized, as shown in FIG. 2C. FIGS. 3-4 show some embodiments of poly(phenyleneethynylene)s of the present invention, as described further herein. In another embodiment, poly(phenylenevinylene)s may be synthesized using methods known in the art, including anionic polymerization conditions, condensation polymerization conditions (e.g., Wittig, Horner, etc), and the like. Oligomers of the present invention may be synthesized using similar polymerization conditions. Alternatively, a step-wise synthesis may be employed, as shown in FIG. 7, further described herein.

In some embodiments, the conjugated materials (e.g., polymers or oligomers) of the present invention exhibit relatively high molar extinction coefficient ($\epsilon$=40,000 per mole polymer repeat unit; 1.5 M repeat unit concentration in a solid particle), relatively high quantum yield (0.4-0.6 in solid film), narrow line width, and resistance to photobleaching. Conjugated materials of the invention may also display substantially reduced (e.g., substantially no) long-term toxicity to a living cell. The chemical composition and the molecular weight of the conjugated polymers and oligomers may dictate their form and morphology. Owing to the versatility of synthetic and polymer chemistry, the resulting molecular weight and composition of conjugated polymers or oligomers may be easily controlled. In particular, control of the polymer or oligomer composition may allow facile control of the particle hydrophilicity and accessible chemical functional groups for conjugation.

The properties of the conjugated polymers or oligomers may be tuned based on the monomer(s) or combination of monomers used. Those skilled in the art would recognize what types of monomers (or combinations thereof) would afford a particular, desired property, such as solubility and biocompatibility, as described herein, or a specific emission wavelength. For example, the monomers may be substituted with electron-poor groups, such as acyl, carboxyl, cyano, nitro, sulfonate, or the like, or the monomers may install electron-poor aryl groups (e.g., heteroaryl groups, such as benzothiadiazole, and the like) in the backbone of the polymer, such that the conjugated polymers or oligomers exhibit fluorescence emission at shorter wavelengths. electron-donating groups. In other embodiments, the monomers may be substituted with electron-rich groups, such as amino, hydroxy, alkoxy, acylamino, acyloxy, alkyl, halide, and the like, or the monomers may install electron-rich aryl groups in the backbone of the polymer, such that the conjugated polymers or oligomers exhibit fluorescence emission at longer wavelengths. In some embodiments, the polymer may tailored to advantageously have a large Stokes shift, wherein the fluorescence spectrum is observed at a substantially longer wavelength than the excitation spectrum. In some embodiments, an electron-rich monomer may be co-polymerized with an electron-poor monomer to produce polymers having longer wavelength emission.

Figure 3A:
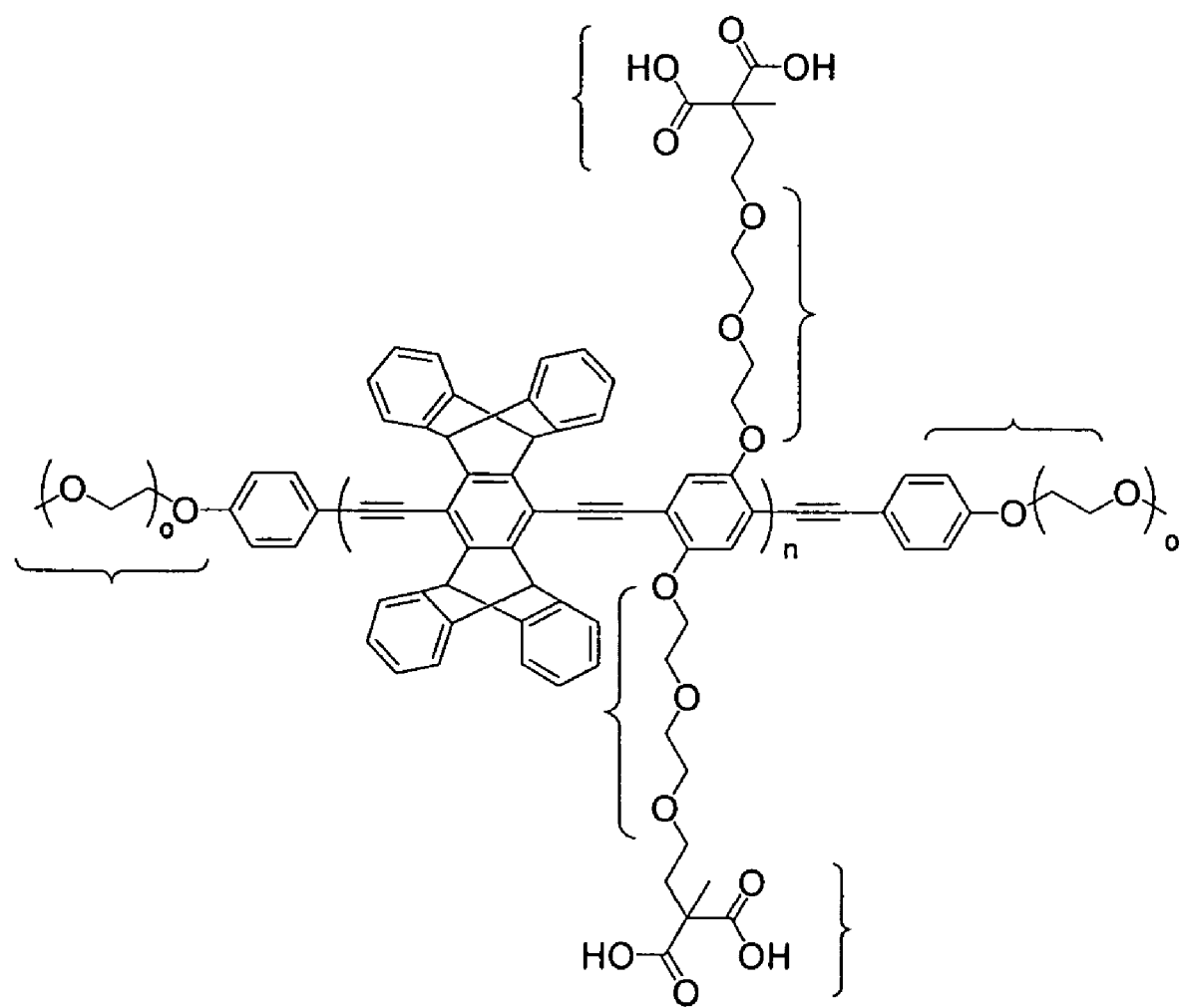
FIG. 3 shows examples of conjugated polymers and oligomers according to some embodiments of the present invention, including (A) a polymer that is emissive at 460 nm, (B) a polymer that is emissive at 670 nm, and (C) a polymer that is emissive at 530 nm.
Figure 3B:
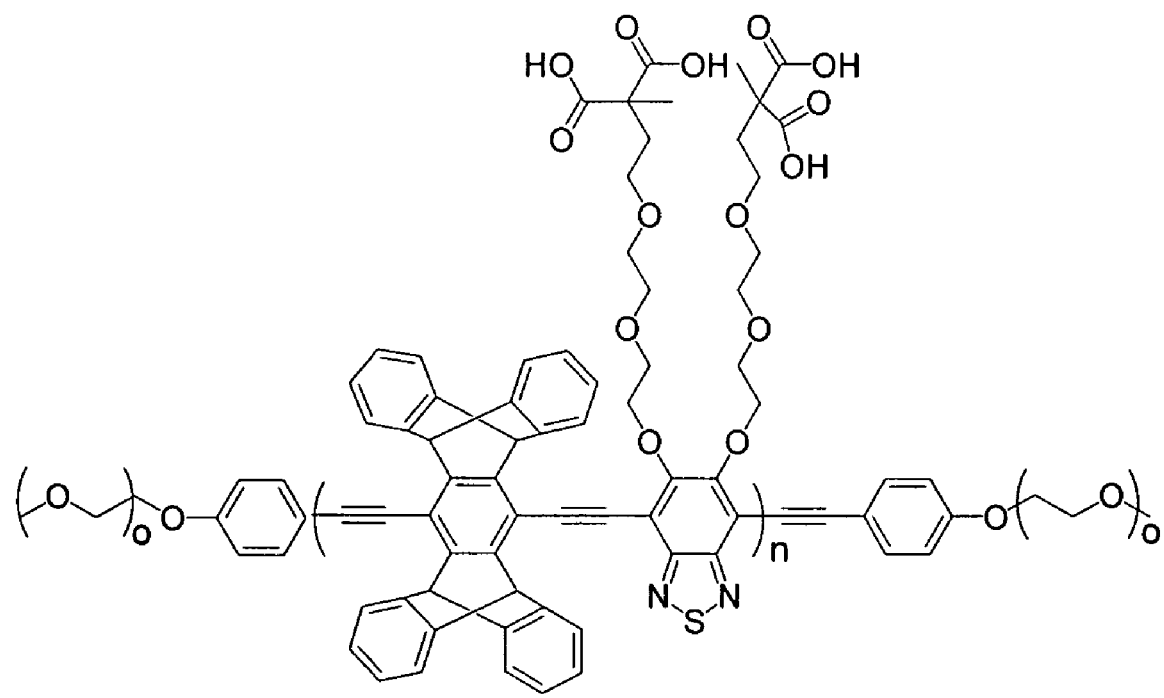
Figure 3C:
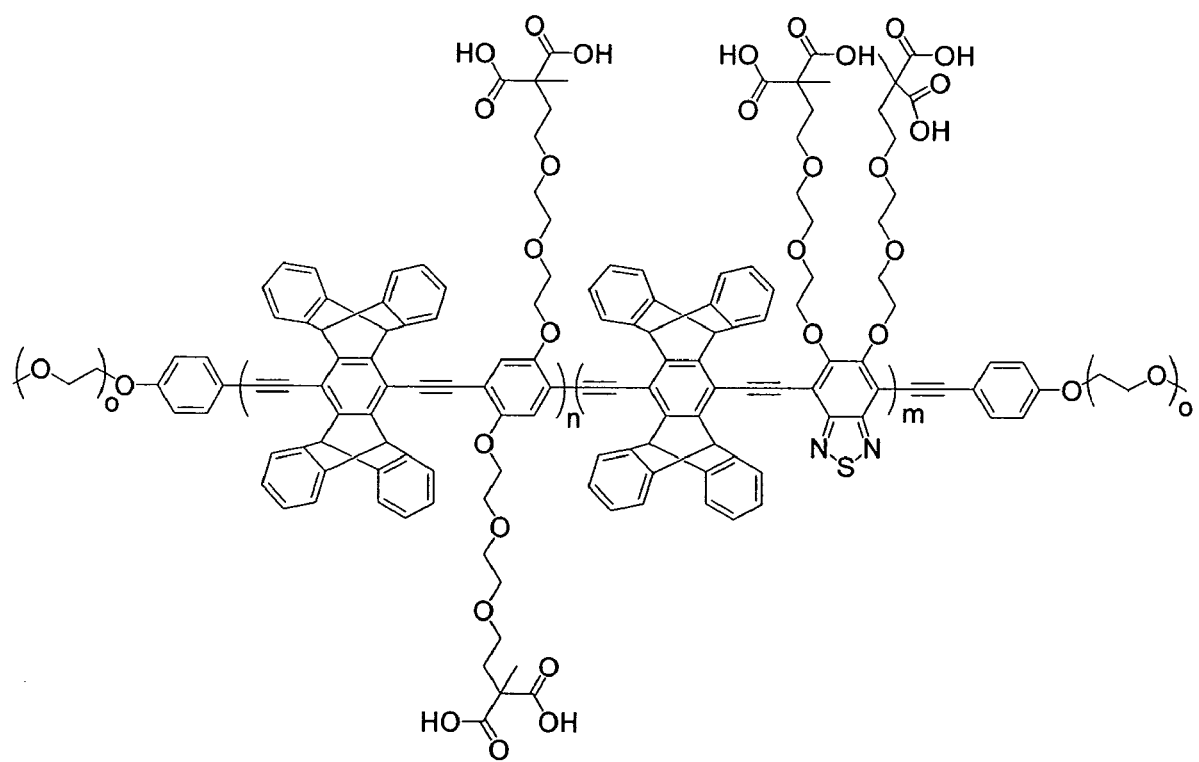
Figure 4:
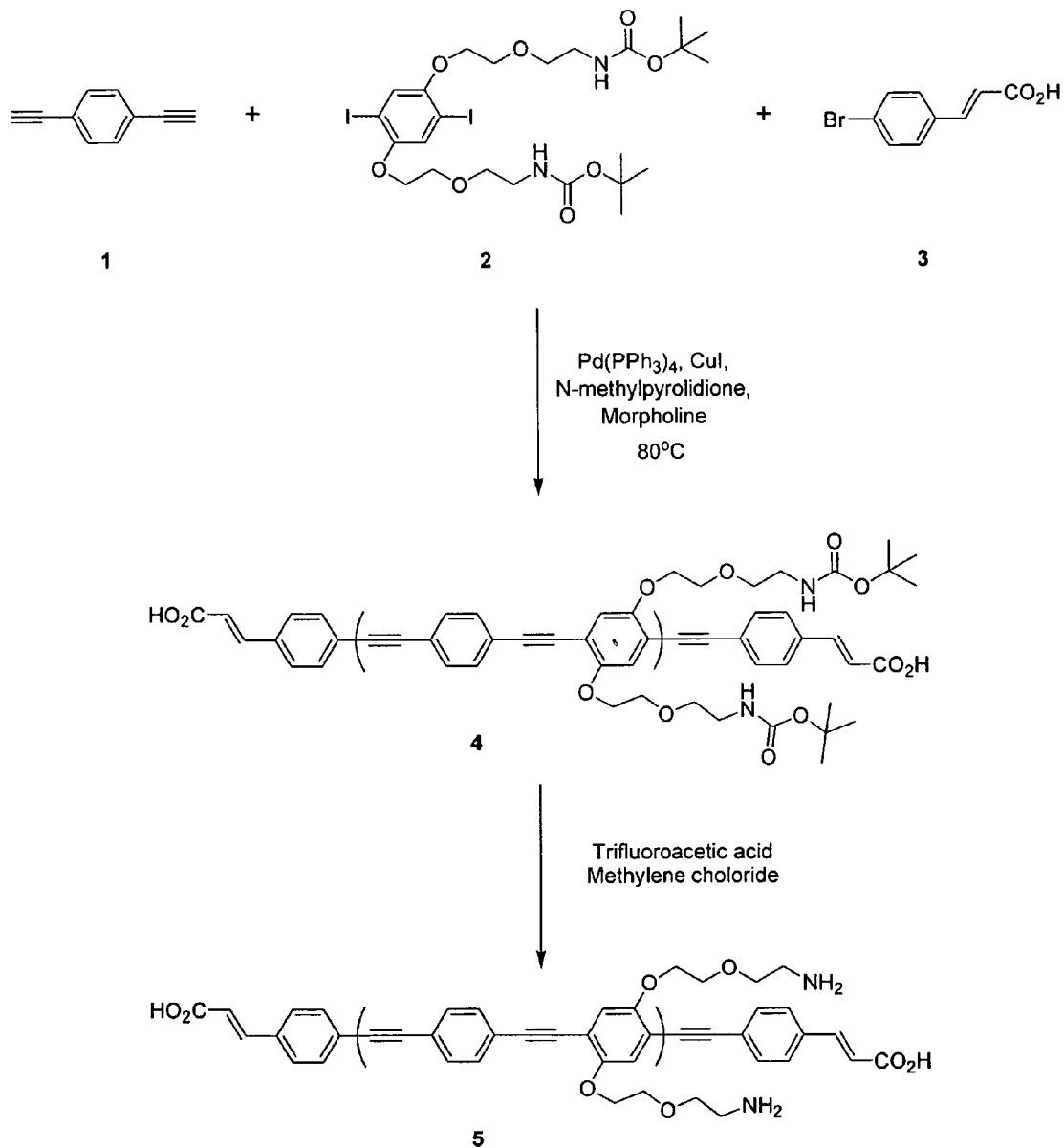
FIG. 4 shows the synthesis of two conjugated polymers according to one embodiment of the invention.

The polymers shown in FIG. 3 may illustrate the tunability of conjugated polymers of the invention. FIG. 3A shows one embodiment of the invention, wherein polymerization of an electron-rich monomer comprising a pentiptycene and a PEG-substituted phenyl group may produce a polymer having an emission at 460 nm. In another embodiment shown in FIG. 3B, polymerization of an electron-poor monomer comprising a pentiptycene and a PEG-substituted benzothiadiazole may produce a polymer having an emission at 670 nm. In order to synthesize a polymer having an emission wavelength between 460 nm and 670 nm, co-polymerization of the monomer comprising a pentiptycene and a PEG-substituted benzothiadiazole group with the monomer comprising a pentiptycene and a PEG-substituted phenyl group may be performed, producing a polymer having an excitation at 420 nm and an emission at 530 nm. (FIG. 3C) In this case, the emission wavelength may be attributed to intermolecular charge transfer between the electron-poor benzothidiazole and electron-rich alkoxyphenylene units.

In some embodiments, the conjugated polymer or oligomer comprises a sterically bulky monomer that may aid in preserving the optical properties of the polymer or oligomer, even in the solid state. That is, the use of sterically bulky monomers may prevent adjacent or nearby neighboring molecules from interacting with each other through, for example, $\pi$-stacking, to cause a decrease in emission. Examples of bulky monomers may include monomers comprising surfactants, proteins, or sterically large organic groups such as pentiptycenes having five arene planes, triptycenes having three arene planes, or other iptycene and iptycene-related moieties. By minimizing the intermolecular $\pi$-$\pi$ interactions between nearby or adjacent polymers, the shape of the emission spectra may remain substantially the same as the conjugated polymers are formed into particles. As a result, the photophysical properties of the conjugated polymer or oligomer may not be determined by molecular weight but will be altered by the electronic nature of monomer. Therefore, a conjugated polymer may have intrinsic flexibility regarding nanoparticle fabrication and size selection.

In some embodiments, the polymer may comprise one monomer (e.g., a "homopolymer"). In some embodiments, the polymer may comprise a plurality of monomers. In some embodiments, the polymer may comprise more than one monomer (e.g., a "copolymer") with the monomers forming the copolymer arranged in a random fashion. In one embodiment, the polymer may comprise more than one type of monomer block (e.g., a "block co-polymer"). In addition, other polymeric arrangements may be included, such as branched, grafted, star, and the like. The ratio of the monomers used may be varied according to a particular application. For example, in one embodiment, there may be two monomer types, having a 50:50 ratio. In other embodiments, the ratio between the two monomer types may be 1:2, 1:3, 1:5, 1:10, 1:50, 1:100, 1:1000, or 1:10,000. Any monomer type may be the most prevalent monomer type. Other ratios of the monomer types may also be possible. For example, in a triblock polymer, there may be three monomers having any distribution ratio, for example, 1:1:1, or 1:2:3.

Monomers of the present invention may be synthesized by methods known in the art. Some illustrative embodiments of the syntheses of monomers (e.g., dihaloaryl monomers), are shown in FIGS. 4-6, as further described herein.

In some embodiments, the conjugated polymers/oligomers may be appended with various pendant groups (e.g., side chains) attached to the backbone to tune properties such as solubility and cell permeability, for example, of the conjugated polymer or oligomer. In some embodiments, the pendant group is hydrophilic. In some embodiments, the pendant group comprises a charged moiety. In some embodiments, poly(ethylene glycol) (PEG) units may be introduced as side chains for enhancing organic solubility of the resulting polymer. In one set of embodiments, the conjugated polymer or oligomer comprises PEG groups. PEG-coated surfaces are biocompatible, nonimmunogenic, nonantigenic, and protein-resistant because PEG has uncharged hydrophilic residues and a very high surface mobility leading to high steric exclusion. In addition, PEG can be dissolved in both polar and nonpolar solvents and has high solubility in cell membranes; therefore, PEG-coated particles can cross cell membranes and ease the internalization process.

PEG groups may also assist stabilization of nanoparticles formed by conjugated polymers/oligomers, minimizing hydrophobic aggregation of particles. In some embodiments, the conjugated polymer/oligomer is amphiphilic, having a hydrophobic backbone surrounded by hydrophilic sidechains. The amphiphilic nature of the polymer allows it to be transformed into a single-chain collapsed particle or a pseudo-micelle in solution, depending on the nature of the solvent and polymer. In a certain embodiments, the hydrophilic exterior of the conjugated polymer/oligomer may facilitate penetration of the cell membrane and reduce the hydrophobic nonspecific interaction with substances from inside the cells.

Other examples of pendant groups (or side chains) include groups comprising an alkyl group, an alkoxy group, an aromatic group, a carbonyl group, a sulfate, a sulfonate, an amine, an alcohol, a thiol, a cyanate, substituted derivatives thereof, or combinations thereof.

In one embodiment, the side chains may comprise one or more charged moieties. The charged group may be any charged group, such as a sulfate, a phosphate, a carboxylate, or an amine group, such as a quaternary amine, or the like. In addition, the charged moiety may be altered by changing the environment in which the molecule is located, for example, by changing the pH, ion concentration, or temperature of the surrounding media. In other embodiments, the side chains may comprise a bioconjugation moiety. As used herein, "bioconjugation moiety" refers to a functional group or precursor thereof that is able to form a covalent bond with a biological entity, such as a biological recognition group. In some embodiments, the bioconjugation moiety is placed at the terminal end of a side chain of the polymer. In some embodiments, the side chain comprises a bioconjugation moiety precursor which can be converted into a bioconjugation moiety in one step, such as a deprotection step. Suitable protection and deprotection methods are known to those of ordinary skill in the art.

In one embodiment, the bioconjugation moiety may be a carboxylate group, which can be activated to form an amine-reactive group via carbodiimide chemistry or in situ activation reagents, such as 2-(1H-benzotriazole-1-yl)-1,1,3,3-tetramethyluronium hexafluorophosphate (HBTu) or N-hydroxybenzotriazole.H$_2$O(HOBt), for example. In one embodiment, the bioconjugation moiety may be a maleimide group, which may form a covalent bond with a thiol on, for example, a cysteine group. In one embodiment, a malonic ester group may be incorporated at the terminal end of a side chain to couple peptides or nucleic acids to the polymer or oligomer. The malonic ester may be activated, for example, by hydrolysis under aqueous basic conditions followed by conversion of the carboxylates to an amine-reactive or thiol-reactive group.

In some embodiments, the conjugated polymers/oligomers may be appended with various ligands, wherein the ligand may be selected to specifically bind a protein within a cell. In some cases, the ligands may further comprise a fluorophore, such as a small molecule fluorophore. Ligands that specifically bind proteins are known in the art and may be attached to conjugated polymers/oligomers of the invention using methods as described herein. Such materials would be useful in the fluorescent tagging of proteins within cells.

In some embodiments, polymers and oligomers of the present invention comprise an end-capping group. For example, the polymers shown in FIG. 3 each comprise a PEG-substituted phenyl group as an end-capping group. The term "end-cap" or "end-capping group" is known in the art and refers to a monomeric group which is placed at the terminal end of a polymer. In some embodiments, the end-capping group may be used to tune the electronic and/or optical properties of the polymer. Also, the end-capping group may be used to tune the solubility of the polymer (e.g., PEG groups, charged groups). Furthermore, end-capping may provide an efficient way to obtain a low molecular weight polymer. In some cases, the end-capping group may be alkyl, cycloalkyl, heteroalkyl, aryl, heteroaryl, substituted derivates thereof, or combinations thereof. In some cases, the end-capping group is electron-withdrawing. Examples of suitable end-capping groups include phenyl, pyridinyl, anthracenyl, phenylenevinylene, phenyleneethynylene, and substituted derivatives thereof.

In some embodiments, the conjugated polymers or oligomers of the invention comprise a conjugated backbone, pendant side chains, a biological recognition entity, and at least one end-capping group.

In one embodiment, the polymer or the oligomer may comprise the structure,

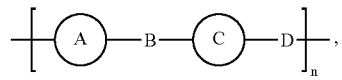

wherein n is at least 1, at least one of A and C comprises an aromatic group, and B and D are independently absent, a double bond, or a triple bond. In one embodiment, at least two of A, B, C, D are in π-electron communication.

In one embodiment, the polymer or the oligomer comprises the structure,

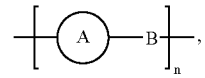

wherein n is at least 1, A comprises an aromatic group, and B is a double bond, or a triple bond. In one embodiment, A and B are in π-electron communication.

In some embodiments, the conjugated materials may form collapsed particles, pseudo-micelles, or the like. In some cases, the polymer or oligomer has a largest dimension no greater than about 100 nm, no greater than about 80 nm, no greater than about 60 nm, no greater than about 40 nm, no greater than about 20 nm, no greater than about 10 nm, or no greater than about 5 nm. A "particle," as used herein, refers to an isolated, independent structure, including at least one molecule. In some embodiments, the conjugated polymer or oligomer may form a particle having a size of less than 100 nm, preferably less than 80 nm, more preferably less than 60 nm, more preferably less than 40 nm, and still more preferably less than 20 nm. "Particles" of the invention can include aggregates of molecules. For example, the molecules within the particle may or may not be covalently bound to each other, e.g. they may be aggregated due to ionic or van der Waals interactions, hydrophobic forces, steric interactions of entangled molecules, and the like. Alternatively, some or all molecules defining a particle can be covalently attached to adjacent molecules.

Conjugated polymers or oligomers of the invention may be formed into particles using any suitable technique known in the art, such as spray-drying, nebulization, phase inversion, or the like. In one set of embodiments, the particles are formed using phase inversion techniques, for example, by using temperature changes or solvent inversion. In temperature phase inversion, a change in temperature forces the polymers to form an aggregated state as a dispersed particle. As used herein, "dispersion," "dispersed particles" and similar terms are given their ordinary meaning as understood in the art, where the dispersion consists of particles in a medium, in which the particles and the materials forming the particles (e.g., a polymer) are generally insoluble in the medium, but typically are unable to precipitate out of the medium due to their size or other particle/particle interactions that prevent coalescence. The medium containing the particles may be any medium, for example, a fluid, such as water or an organic solvent; a gel, such as a hydrogel; a polymer, for example, polystyrene or an optically clear polymer; or a glass, for example, $SiO_2$ or other formulations having irregular molecular structures. In a particular embodiment, the medium is water or water containing other ions or molecules, for example, as in a salt solution such as saline or potassium chloride solution. Simple phase inversion condition may offer a tremendous advantage in ease of fabrication. Phase inversion can be a relatively simple and inexpensive process compared to other processes, such as high-temperature precipitation of metal chalcogenides, for example, where the precipitation kinetics must be carefully controlled in order to assure the narrow size distribution of particles In a particular embodiment, conjugated polymers of the invention may be fabricated into collapsed particles by phase inverse precipitation utilizing the solubility difference of the polymer in various solvents. The conjugated polymer may have any size or molecular weight suited for a particular application. Particle size may controllable through the choice of the ratio of monomers, the nature of monomers, and the salt concentration of media.

One advantage of the present invention may be that, in some embodiments, the emission of the conjugated polymer or oligomer is not dependent on the size of the nanoparticle. Quantum confinement of excitons within the inorganic nanoparticle provides precise control over the energy of the particle emission. This constrains nanoparticle manufacture as one must carefully control the size and, more importantly, the size distribution of particles in order to produce particles with a reproducible, narrow emission. In contrast, some embodiments of the invention employ materials designed to minimize intermolecular π-π interactions. Thus, as a solvated polymer chain may be condensed to a solid, the shape of their fluorescence emission may change little and, although some attenuation may be seen in quantum efficiency, the materials may remain highly fluorescent. This feature may be advantageous since the emission of the material may not be dependent on nanoparticle size. This significantly relaxes constraints on nanoparticle fabrication and processing as polydispersity in nanoparticle size will have little effect on the polymer emission. In some embodiment, only 7-10 monomeric units may be needed to preserve minimum photophysical properties.

The conjugated polymers and oligomers of the present invention may further comprise a biological recognition entity. As used herein, a "biological recognition entity" may be any biomolecule capable of having a recognizing interaction with a cell, cell membrane, or species associated with a cell. A "recognizing interaction" typically will involve biological specific or non-specific binding such that the recognition entity will recognize and interact with a cell, cell membrane, or species associated with a cell uniquely, that is, reacting with that cell or species preferentially rather than with other similar cells or species. Those of ordinary skill in the art understand this terminology and how to select recognition entities suitable for use in the context of the present invention.

In one embodiment, the biological recognition entity is a peptide (e.g., a cell-penetrating peptide). Examples of suitable peptides include PPKKKRKVPPKKKRKV from SV40 large T antigen protein, an oligomeric peptide sequence YGRKKRRQRRR, protein transduction domain (PTD) from the human immunodeficiency virus TAT protein, and random peptide sequences of EPPLSQEAFADLLKKK, other synthetic peptides, natural peptides, cationic peptides, and peptides derived from viral, inset, or mammalian proteins endowed with membrane translocation properties. Short peptides derived from protein-transduction domains are known to achieve internalization in most cell types. In some embodiments, the mechanism of cellular internalization of cell-penetrating peptides may involve endocytosis.

In some embodiments, the biological recognition entity is a protein. There are a numerous proteins which can traverse the cell membrane via the process of protein transduction and reach the nucleus while retaining their biological activity. In some embodiments, short-transduction domains are responsible for the cellular uptake of these proteins.

In some embodiments, the biological recognition entity is a short interfering RNA (siRNA). Small interfering RNA (siRNA) are a class of 20-25 nucleotide-long RNA molecules that may interfere with the expression of genes. For example, siRNA molecules can bind with proteins to form a unit called the RNA-induced silencing complex (RISC) that suppresses the expression of the gene it corresponds to in the viral genome silencing the gene from which the siRNA is derived.

In some embodiments, the conjugated polymer or oligomer may be associated with a support material to form a composite material. The composite material may have a surface to which the conjugated polymers or oligomer can be bound, for example, by covalent bonds. For example, the composite material may be a polymer resin possessing surface chemical functionalities that may form covalent bonds with the conjugated polymer or oligomer. In some cases, the conjugated polymer or oligomer may be adsorbed to the composite material, such as silica. Examples of composite materials include substances such as metals, metal oxides such as silica, titanium oxide, zirconium oxide, chromium oxide, and iron oxide, ceramics such as silicon nitride and aluminum nitride, resins, or glasses. Synthetic resins may include polystyrene, polysulfone, polyethersulfone, polyolefins (e.g., polyethylene and polypropylene), polyacrylates, polyvinyl acetate (and partially hydrolyzed versions thereof), ring-opening polymers, polyethers, epoxide polymers, polyesters, polyamides, phenol-formaldehyde polymers, heterocyclic polymers, polysiloxanes, polyphosphazenes, and the like.

The materials and methods of the present invention may be advantageous for use in the emission-based study of biological systems. The conjugated materials of the invention adsorb light strongly at the excitation wavelength and emit with a high quantum yield and large Stokes shift, making the conjugated polymer or oligomer photostable under experimental conditions due to photophysical properties that enable sensitive detection with high resolution. Conjugated polymers and oligomers of the invention may exhibit excellent quantum efficiency and high photostability toward extensive irradiation of light. In addition, the emission profile may show little difference toward pH and temperature changes. Also, the relative ease of fabrication allows for a wide range of materials to be synthesized to suit a particular application. Particle size can be modulated by adjusting both polymer properties, such as solubility, charge density, and molecular weight, and precipitation conditions, such as concentration, pH, and salt concentration. The photophysical properties of the conjugated polymer and oligomers are not dependent on their size. Rather, the emission wavelength may be determined by the nature of the monomer used for polymerization. Furthermore, since the conjugated materials used herein may be all-organic materials formed from aqueous media, they may be substantially non-toxic or less toxic to living cells compared to, for example, heavy metal quantum dots.

EXAMPLES

Example 1

Synthesis of Monomers with Terminal Malonic Esters

Figure 5A:
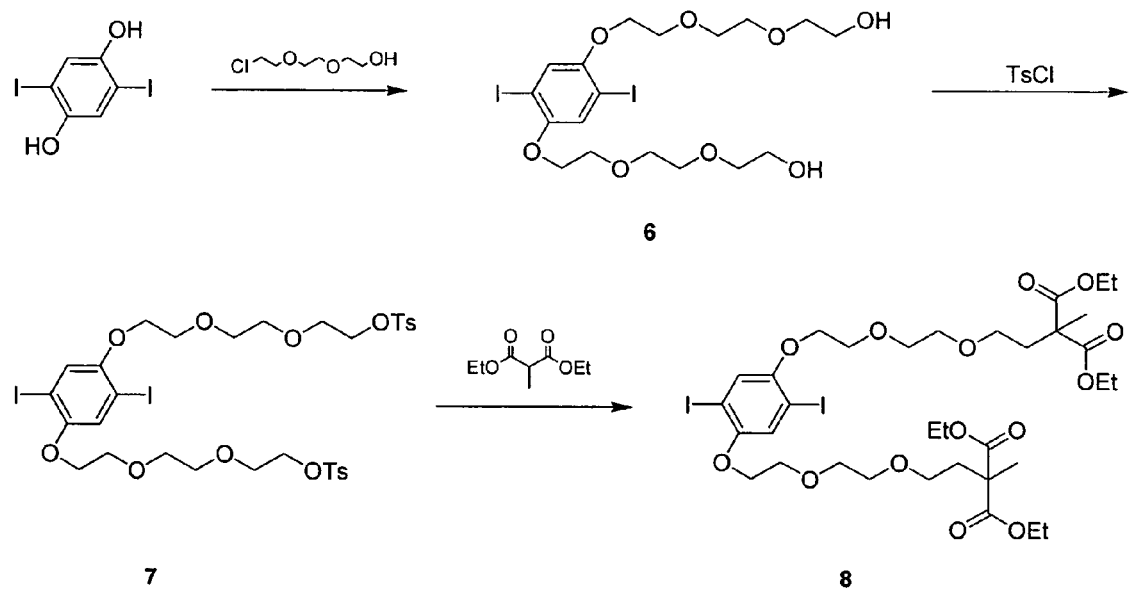
FIG. 5A and FIG. 5B show the syntheses of monomers comprising terminal malonic esters that may be used in the present invention.

FIG. 5 shows examples of the syntheses of monomers having malonic esters at the terminal end of PEG side chains. FIG. 5A shows the synthesis of di-iodide monomer 8 having para-substituted side-chains. First, the phenolic groups of diiodohydroquinone may be alkylated with hydroxy-terminated PEG groups to give compound 6. Conversion of the terminal hydroxyl groups to tosyl groups gives compound 7, followed by substitution of the tosyl groups with malonic esters to afford monomer 8.

Figure 5B:
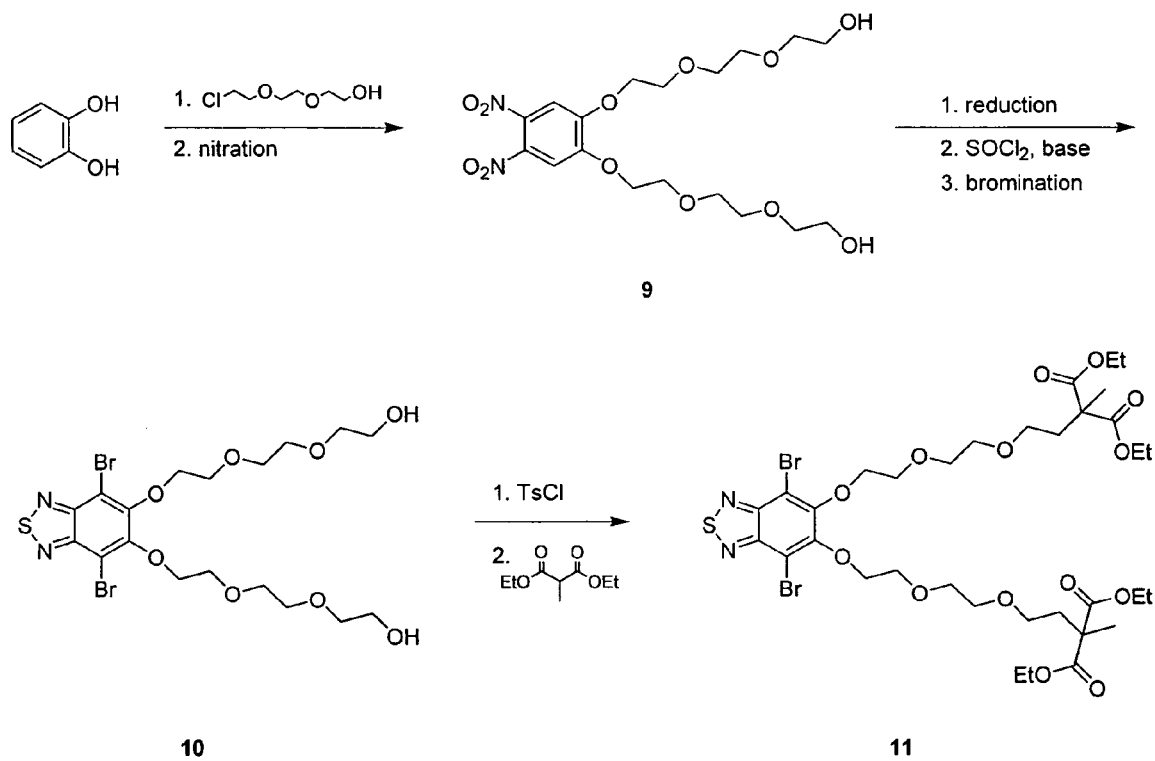
Figure 6:
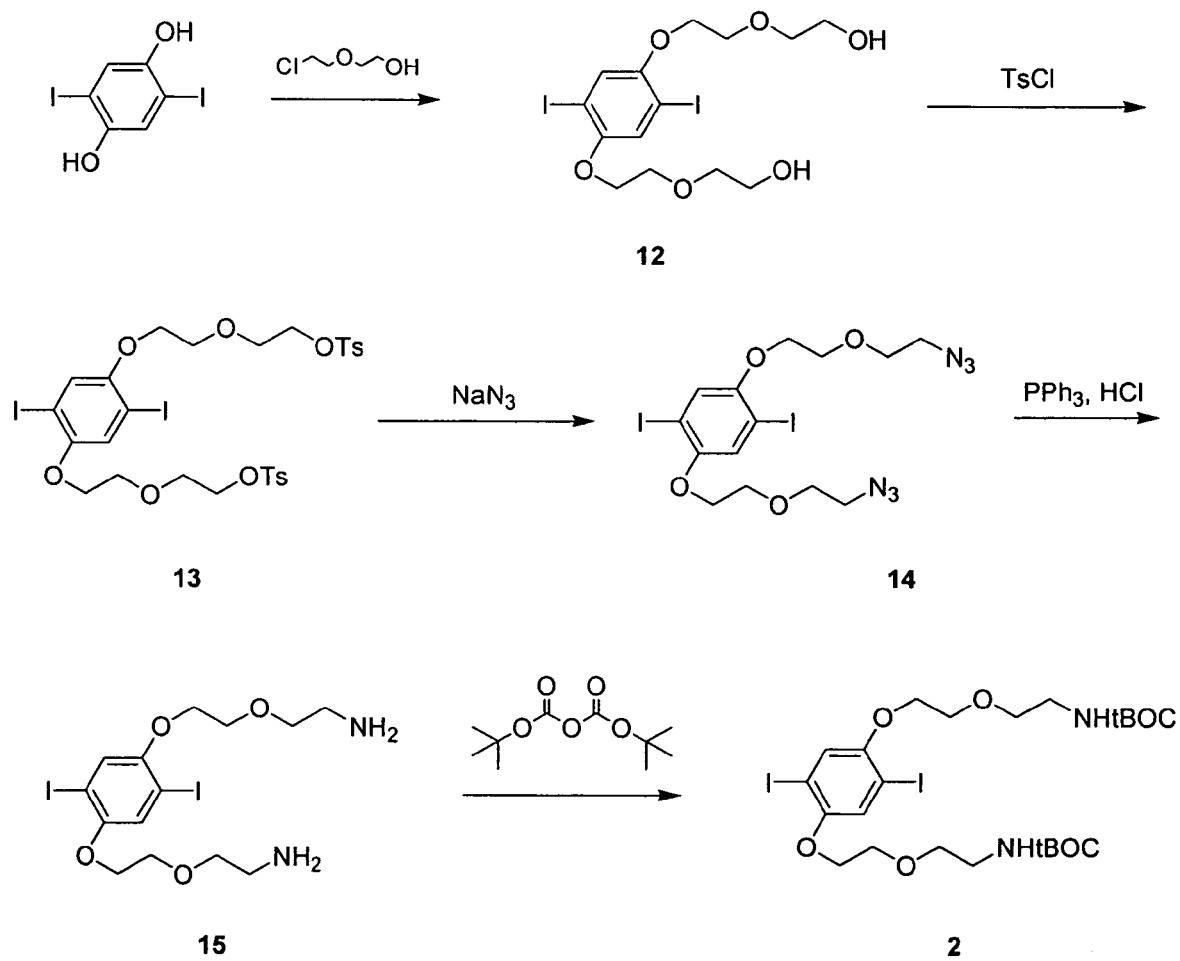
FIG. 6 shows the synthesis of an amine-terminated monomer that may be used in the present invention.

FIG. 5B shows the synthesis of dibromobenzathiadiazole monomer 11 having meta-substituted side chains containing malonic ester groups. Dihydroxybenzene may be first alkylated with hydroxy-terminated PEG groups and then nitrated using methods known in the art to give di-nitro compound 9. Reduction of the nitro groups followed by treatment with thionyl chloride would afford benzothiadiazole 10. Subsequent bromination and installation of the terminal malonic esters groups as described above would afford the dibromobenzathiadiazole monomer 11.

Example 2

Synthesis of 12

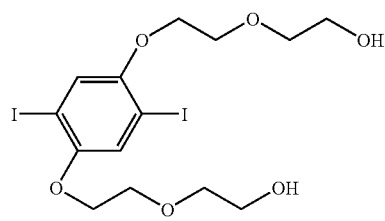

To a triple-necked 2 L round bottom flask was added diiodohydroquinone (80.0 g, 220 moles, 1 eq.), potassium carbonate (122.3 g, 880 moles, 4 eq.), and acetone (1000 mL, 1.0 g/12.5 mL, [0.22 M]). The central neck of the flask was equipped with a mechanical stirrer while one side neck was equipped with a rubber septum and the other was equipped with a reflux condenser, rubber septum and a bubbler. The suspension was stirred and sparged with Argon for 30 minutes. The rubber septum was briefly removed and sodium iodide (1 g) was added to the reaction mixture. The rubber septum was replaced and the suspension was sparged again with Argon for an additional 20 minutes. To a 250 mL dripping column a mixture of chloroethoxy ethanol (94 mL, 109.6 g, 880 moles, 4 eq.) and acetone (106 mL) was added and this column replaced the rubber septum on the triple necked round bottom flask. The flask was flushed with argon for 20 minutes. Argon flushing was then discontinued and the reaction mixture was heated to reflux. The chloroethoxy ethanol/acetone mixture was then added drop wise into the reaction mixture (ca. 1 drop/2.5 seconds).

After seven days of stirring under reflux the reaction mixture was filtered and the acetone solvent was evaporated to obtain a dark brown slurry which later condensed into a solid. The solid that had been initially filtered off was ground in a mortar and pestle with acetone to remove additional dissolved product, and this was evaporated and combined with the other product solids. These combined solids were ground in a mortar and pestle with water to remove impurities. The liquid portion was then removed by filtration and discarded, the remaining solid was rinsed with water, and the resulting brown solid was dried by vacuum over the weekend. Yield=75.2 g (64%). Product has an $R_f$ value of 0.50 in 100% ethyl acetate; 0.08 in hexanes 1, ethyl acetate 1. Solubility=1 g/20 mL methanol, 1 g/35 mL acetone, less then 1 g/65 mL ethyl alcohol. Not very soluble in hexanes or water. $^1$H NMR (400 MHz, CDCl$_3$) 2.18 (t, 2H), 3.74 (m, 4H), 3.79 (m, 4H), 3.91 (m, 4H), 4.14 (m, 4H), 7.28, (s, 2H). (NMR ref. AC 1056)

Example 3

Synthesis of 13

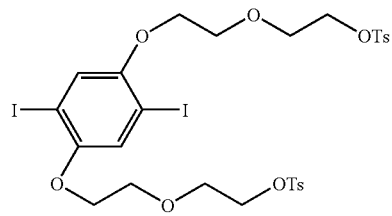

To a 500 mL round bottom flask equipped with a septum, bubbler and stir bar was added 1 (10.0 g, 18.6 mmol, 1 eq.) and 200 mL of dichloromethane (20 mL/g). The flask was sparged with Argon for 10 min. with stirring. Triethylamine (8.2 mL, 111 mmol, 6 eq.) was then poured in and reaction mixture was sparged for 10 more minutes followed by the addition of p-TsCl (10.6 g, 55.6 mmol, 3 eq.) and 10 more minutes of sparging. Argon sparging was then discontinued and reaction progressed over night at room temperature.

The reaction mixture was cooled, and then washed with 600 mL of 1M HCl. Organic layer was combined and then washed in 250 mL of brine and water. Organic layer was then dried over magnesium sulfate, and concentrated. To this crude product was added 150 mL of methanol and a stir bar and the flask was heated to boiling with stirring. The suspension was then suction filtered to obtain a brown powder. Yield=5.4 g (34%). Product has an $R_f$ value of 0.62 in Hexanes 1, Ethyl Acetate 1; 0.20 in Hexanes 2, Ethyl Acetate 1. Product is soluble in DMF or acetone. Not very soluble (much less then 1 g/450 mL) in methanol. $^1$H NMR (400 MHz, CDCl$_3$) 2.45 (s, 6H), 3.84 (m, 8H), 4.03 (m, 4H), 4.22 (m, 4H), 7.19 (s, 2H), 7.33 (d, 4H), 7.82, (d, 4H).

Example 4

Synthesis of 14

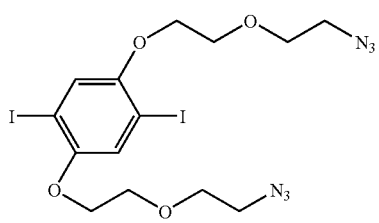

A stirred suspension of 2 (12.0 g, 14.18 mmol) in 70 ml anhydrous DMF was treated with sodium azide (9.8 g, 141.8 mmol) under argon. The mixture was stirred in an oil bath held at 60° C. for 5 hrs. Reaction progress was monitored by TLC (2:1 Hex/EA) until completion (starting material consumed).

The reaction mixture was then removed from heat source, diluted with 700 ml diionized water and extracted with methylene chloride (3×250 ml). The combined organics were dried over Na$_2$SO$_4$, filtered and concentrated down. Purification on a silica gel column with 2:1 hexane/ethyl acetate as eluent afforded pure product (7.0 g, 83.9%).

Example 5

Synthesis of 15

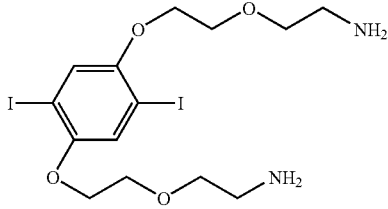

Under argon, 70 ml of anhydrous THF was cannulated to 3 (6.48 g, 11.0 mmol) in a flask. A 6.4 g of triphenylphosphine was quickly added into the flask under argon environment. The reaction mixture was stirred in oil bath at 60° C. under argon for 16 hrs until no starting material noticed by TLC (2:1 Hexane/Ethyl Acetate).

A 100 ml of 2 M HCl (aq) was added to the reaction mixture, and then the flask was stirred in the oil bath for 3½ hrs. THF was removed by rotary evaporation after pH adjustment to 1 (by HCl). The resulting mixture was then extracted with ethyl acetate (2×100 ml). The aqueous solution was then basicified with 6 M KOH (aq) and extracted with methylene chloride (4×200 ml) until all product recovered into the organic solvent. All organics containing product (TLC'd in 5% NH$_4$OH/DCM with trace methanol) were combined and concentrated down until a white solid remained. Triturated solid using ethyl acetate and sonication, filtered off white solid and rinsed with ethyl acetate affording a clean white solid (4.3 g, 72%). $^1$H NMR (400 MHz, CD$_3$OD): 7.36 (2H, s), 4.11 (4H, t), 3.83 (4H, t), 3.62 (4H, t) and 2.82 (4H, t)

Example 6

Synthesis of 2

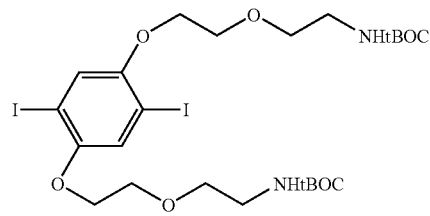

Under argon, 50 ml anhydrous THF was cannulated into 4 (4.3 g, 8.0 mmol) and the flask was stirred. After quick purging with Ar, di-t-butyl dicarbonate (5.0 g, 23.0 mmol) was added increasingly while maintaining argon flow during the addition. The reaction was kept under Ar for 16 hrs at room temperature. Concentrated down reaction mixture produced an off white solid. Product was purified by using silica gel column (eluting with 10% MeOH in 1:1 Hexane/DCM). The material was further purified by crystallization from ethanol. Crystallization afforded a pure white product (3.9 g, 66%). 1H NMR (400 MHz, CDCl3): 7.23 (2H, s), 4.08 (4H, t), 3.82 (4H, t), 3.64 (4H, t), 3.35 (4H, t) and 1.44 (18H, s).

Example 7

Synthesis and Purification of Polymers

General Procedure. All monomers may be synthesized through organic reactions known in the art and purified with known chromatographic methods. Structural characterization may be performed by $^1$H and $^{13}$C NMR techniques. PPE polymers may be synthesized by the palladium catalyzed cross-coupling reaction with diactylene and dihalide monomers. For high molecular weight polymer, the exact molar equivalent amount of monomers may be used. With an end-capping reagent, the molecular weight of the polymer may be decreased, depending on the ratio of end-capping reagent added. Several polymerization reactions with various end-capping ratios (e.g., 1, 2, and 5%) may yield an array of polymers. The molecular weight of PEG may be varied. The use of 7 to 10 repeat units may preserve minimum photophysical properties. Fractionation of the polymer by molecular weight may be carried out using preparative gel permeation chromatography (GPC). The resulting polymer may be characterized by NMR, GPC, UV, and fluorescence spectroscopy.

The polymers may be purified by passing them through membranes of various pore sizes (Amicon). Particles or polymers may be further fractionated by size using flow membrane filtration techniques. Ultra-filtration membranes, with pore sizes from 1-100 nm, may be used for concentrating dissolved molecules (protein, peptides, nucleic acids, carbohydrates, and other biomolecules), de-salting or exchanging buffers, and gross fractionation. Particles may be characterized by UV and fluorescence spectroscopy. Quantum yield of the particles may be measured by comparing quantum efficiency with standard substances. Dynamic light scattering and transmission electron microscopic analysis will be performed to characterize size and shape of the particles.

After purification, dry powder will be obtained for quantification purposes by lyophilizing the solution.

Example 8

Synthesis of Polymer 4

This example illustrates one method of producing one embodiment of a conjugated polymer of the invention. (FIG. 4)

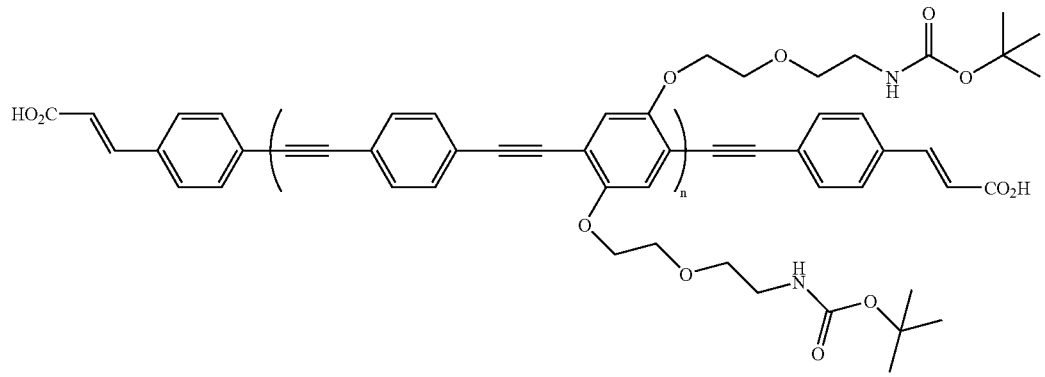

As shown in FIG. 4, under an argon environment, 0.100 g ($7.9\times10^{-4}$ mol) of 1,4-diacetylenebenzene (1), 0.524 g ($7.1\times10^{-4}$ mol) of monomer 2 (Example 6), 0.018 g ($0.8\times10^{-4}$ mol) of 4-bromocinnamic acid (3), ca. 20 mg of Pd(PPh$_3$)$_4$, and ca. 5 mg of CuI were combined. The polymerization solvent (20 ml, N-methylpyrrolidione and morpholine (6:4=v:v)) was degassed for 30 minutes before transferring to the reaction flask. The flask was stirred heated to 80° C. overnight under Ar environment. The reaction mixture was cooled to room temperature, and then precipitated into methanol. The precipitates were collected via centrifugation and dissolved in CH$_2$Cl$_2$, followed by washing with an ammonium chloride solution. The concentrated polymer solution was then transferred into methanol to precipitate the product. The precipitates were collected and dried to yield the product as a yellow powder (75 mg, 15% yield). Gel permeation chromatography (GPC): Mn=$4.1\times10^3$, PDI=1.3.

Example 9

Synthesis of Polymer 5

Polymer 4 (0.030 g) in 4 ml of CH$_2$Cl$_2$ was treated with 1 ml of trifluoroacetic acid (TFA) in room temperature for 3 hours. Upon deprotection of the amine, a viscous oil was formed on the bottom of flask. An access amount of water was added to the reaction mixture, resulting in a yellow solution with some fine powders. The fine powders were filtered off, and the filtrate was dialyzed against water. 0.7 mg/ml of clear solution (20 ml) was obtained. 1 ml of the solution was taken for the NMR sampling through lyophilization and dissolving into D$_2$O. UV $\lambda_{max}$(water)=391 nm; Fluorescence $\lambda_{max}$=436 nm (ex=415 nm).

Example 10

Step-Wise Synthesis of Oligomers

In an illustrative embodiment shown in FIG. 7, a phenyleneethynlyene oligomer may be synthesized by a step-wise synthesis. First, Pd-catalyzed cross coupling between an aryl halide and an acetylene may install the aryl group, followed by another Pd-catalyzed cross-coupling step to install a protected acetylene group. Finally, deprotection of the acetylene group may be carried out using various methods known in the

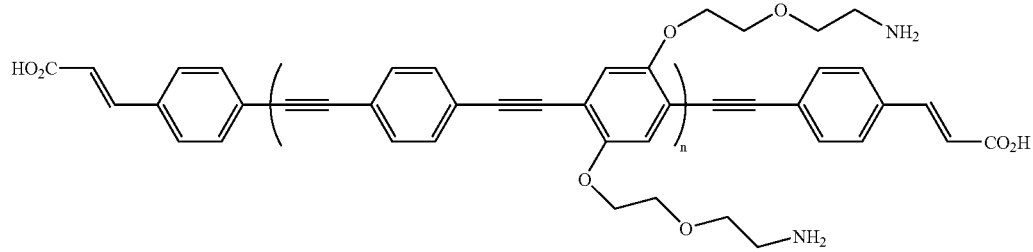

art. These three steps may be repeated as needed to produce an oligomer of a desired length. An end-capping group may also be installed as a final step.

Example 11

Maleimide Coupling Procedure

Figure 8:
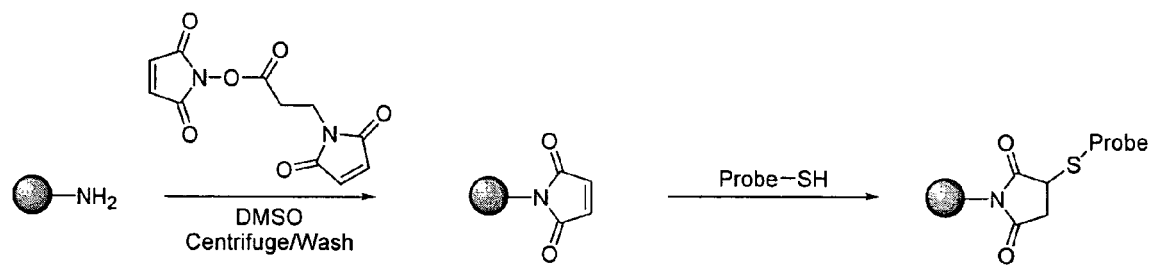
FIG. 8a and FIG. 8b show methods for coupling of nucleic acids to conjugated polymers and oligomers of the present invention.
Figure 8:
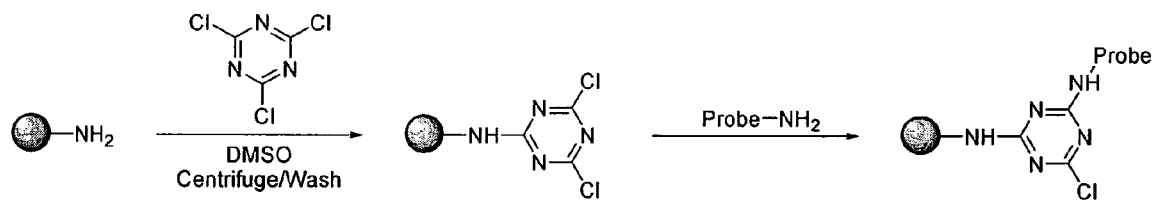

As shown in FIG. 8a, an aliquot of a solution containing an amine-substituted conjugated polymer or oligomer was added dropwise to a vial containing 3-maleimidopropionic acid N-hydroxysuccinimide (MPS) (10 mg) dissolved in a mixture of DMSO (400 μL) and sodium borate buffer (1000 μL, 50 mM, pH 8.2) and mixed for 1-2 hours at room temperature. The mixture was then transferred to an Eppendorf tube and was centrifuged. To remove uncoupled MPS, the mixture was successively washed with ethanol, 5% DMF/ethanol (×2), and ethanol (×2). The resulting particle suspension was then added dropwise to a vial containing thiol-functionalized probe (purified using a NAP chromatography column) and mixed for 8 hours at 40° C. Finally, the material was transferred to an Eppendorf tube, centrifuged, and washed successively with SSPE, SSPE/0.05% SDS, and water to remove uncoupled probe. The resultant polymer-probe conjugate was resuspended in 10×SSPE for subsequent use.

Example 12

Cyanuric Chloride Coupling Procedure

As shown in FIG. 8b, an aliquot of a solution containing an amine-substituted conjugated polymer or oligomer was added dropwise to a vial containing cyanuric acid (10 mg) dissolved in DMSO (400 μL). The reaction mixture was mixed for 1-2 hours at room temperature, transferred to an Eppendorf tube and was centrifuged. To remove any uncoupled cyanuric chloride, wash steps involving ethanol, 5% DMF/ethanol (×2), and ethanol (×2) were performed. The resulting particle suspension (500 μL, 50 mM, pH 8.2, sodium borate buffer) was added dropwise to a vial containing amine-functionalized probe (aliquot dissolved in 500 μL sodium borate buffer) and the mixed for 2-3 hours at 40° C. Finally, the material was transferred to an Eppendorf tube, centrifuged, and was washed with a borate buffer to remove uncoupled probe. The resultant particle-probe conjugate was resuspended in 10×SSPE for subsequent use.

Example 13

Prevention of Non-Specific Binding of the Probe

To prevent non-specific binding, a blocking protocol was developed, involving the addition of glutaric anhydride to the polymer-probe suspension in Example 11 and Example 12, mixing overnight at 30° C., centrifugation, washing (as in Examples 11-12), and resuspension in 10×SSPE for subsequent use.

Example 14

Peptide Coupling: Approach 1

Figure 9A:
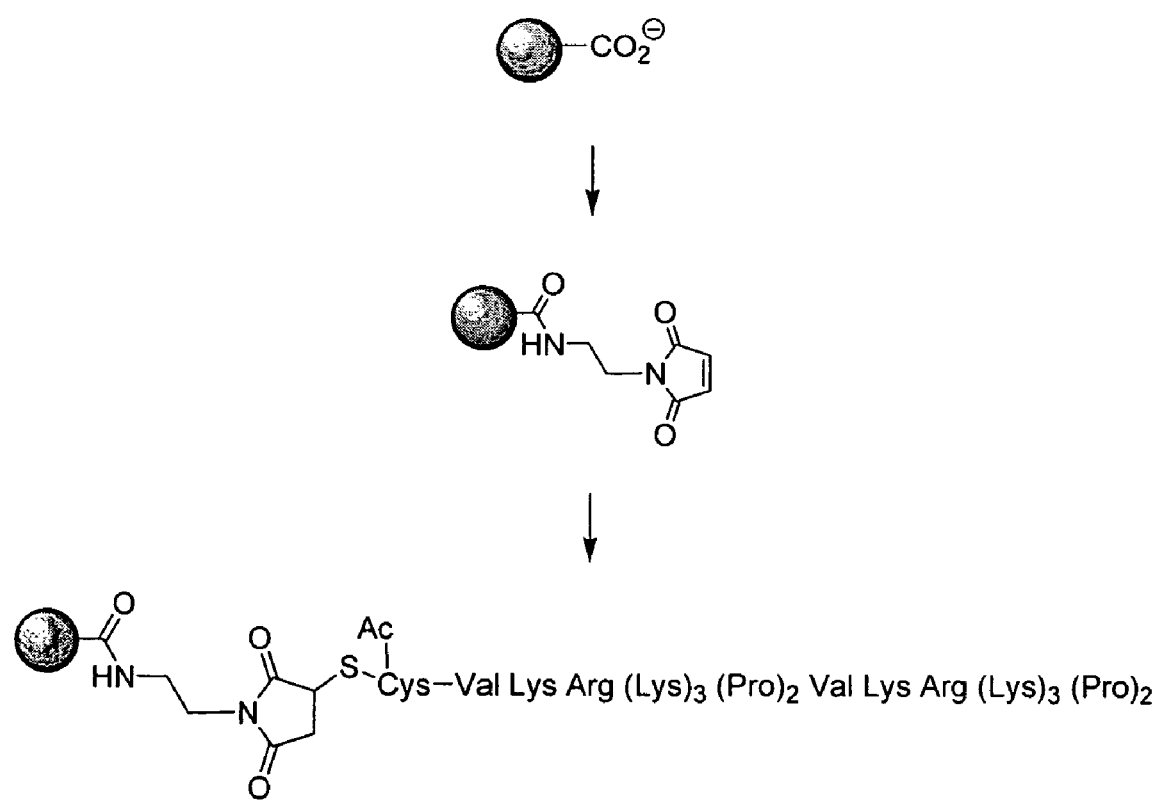
FIGS. 9A and 9B show methods for coupling of peptides to conjugated polymers and oligomers of the present invention.

As shown in FIG. 9A, an N-terminal acetylated peptide (SEQ ID NO: 1), bearing a cysteine at the 1-position, can be reacted with a maleimide functionalized conjugated polymer in water. At least a two-fold excess amount of the peptide can be reacted overnight, and any un-reacted peptide may be removed by adding a scavenger resin derivatized with a maleimido functionality.

Example 15

Peptide Coupling: Approach 2

Figure 9B:
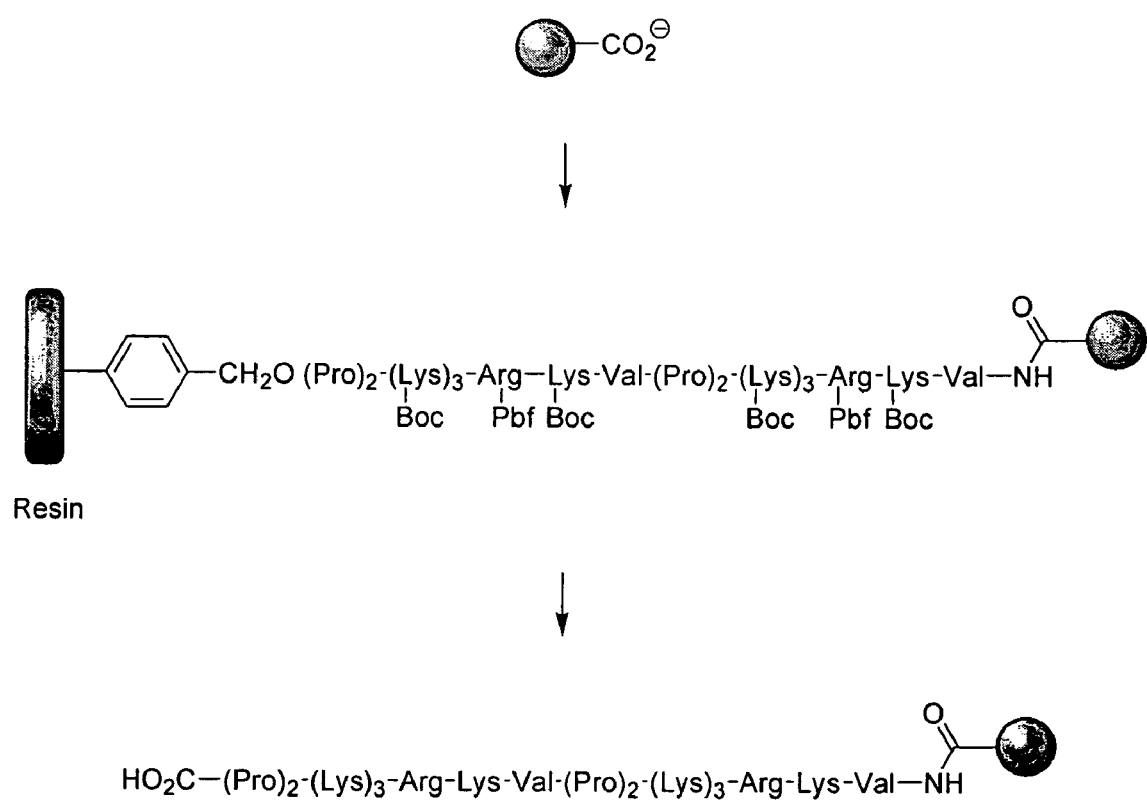

As shown in FIG. 9B, a carboxylate group on a conjugated polymer of the invention may be reacted with an amino group on an N-tenninal valine of a peptide sequence in the presence of the coupling agent, such as carbodiimide. The peptide (SEQ ID NO: 2) may be attached to a resin with the amine groups in the peptide sequence protected by organic protecting groups known in the art. The solution may be mixed overnight, and then the resin will be filtered and washed. The beads may then be treated with TFA to cleave bondage from the support and to deprotect the peptides. The resulting peptide-substituted polymer (SEQ ID NO: 3) may be purified by dialysis against water.

Example 16

Quantification of Peptides

For quantification, commercially available FITC (or Cy5)-labeled peptides can be introduced into the Lys unit during peptide synthesis and can be detected by excitation at 490 nm. The conjugated polymer or oligomer may be selected such that, at 490 nm, the conjugated polymer may not be excited and any background signal may be negligible. By observing the signal from FITC directly, the peptides on the conjugated polymer may be quantified. Elemental analysis on lyophilized conjugated polymers may be conducted. By calculating the atomic percentile of N or S, the amount of peptide per milligram may be quantified.

Example 17

Incubation of Conjugated Polymers/Oligomers with Cells

General Procedure. In order to demonstrate cellular uptake of the conjugated polymer or oligomer in vitro, cell cultures can be grown to sub-confluency in microplate wells, cell culture dishes, and cell culture flasks. A conjugated polymer or oligomer may be added to adherent cell cultures at a range of concentrations and may be allowed to interact with cells for varying lengths of time ranging from 0-24 hours. Cellular uptake of conjugated polymer or oligomer can be monitored at various time points by successive washing with culture medium or buffer to remove excess conjugated polymer or oligomer, followed by direct observation of time point samples with an inverted fluorescent microscope to determine if nanoparticle internalization has occurred. The cell culture conditions may be optimized to enhance the extent and rate of cellular internalization of the conjugated polymer or oligomer. Samples of cell cultures may also be dissociated from any growth support by, for example, trypsin-EDTA treatment.

Cells may be grown, for example, in RPMI-1640 cell culture medium (Invitrogen) supplemented with 10% fetal bovine serum (FBS). Prior to incubation with the conjugated material, the cells may be collected by centrifugation and resuspended in RPMI medium at a cell density of 3×6 cells/mL. Cells may then be incubated with the conjugated polymer or oligomer in solution by mixing 100 μL of the cell suspension with 100 μL of a conjugated polymer or oligomer solution at 37° C. Various concentrations of conjugated materials will be tested. Typically, incubation time may be one hour in a 5% $CO_2$ atmosphere. The membrane and endosome may be stained by using FM4-64 (Molecular Probes, Inc.).

Example 18

Assessment of Cell Toxicity

Initial determination of any potential toxic effects of the conjugated polymer or oligomer may be assessed by monitoring cellular growth characteristics following the addition of the conjugated polymer or oligomer to cell cultures. The cells may be tested upon incubation in flow cytometric assays to determine internalization of the conjugated polymer or oligomer For example, to assess toxicity, staining methods (e.g., propodium iodide or LIVE/DEAD Viability/Cytotoxicity Kit [L-3224], molecular probes) may be used to identify dead cells, if any, caused by exposure of the cells to the conjugated polymer or oligomer. After incubation of cells in a solution containing a conjugated polymer or oligomer for one hour, the cells may then be washed and re-suspended in RPMI medium. The cells may then be placed in an incubator at 37° C. and observed at different time intervals by confocal microscopy method. For confocal microscopy, the cells may be observed at 24-hour intervals for a period of 48 hours. For cytometry, the cells may be observed immediately after the initial incubation with CPBs. The level of cell death may be monitored with control cells by various staining methods, depending on CPB emission. For example, the cell suspension can be supplemented with 2% propodium iodide prior to the measurement. Propodium iodide is a membrane-impermeable dye and does not stain live cells. It can enter dead cells and intercalate into DNA, thereby selectively staining the dead cells red. However, due to broad the spectral feature of propodium iodide, a conjugated polymer or oligomer that is emissive at 460 nm may be used for the staining.

Example 19

Mechanism of Cell Internalization

In order to elucidate the internal uptake mechanism of conjugated polymers or oligomers into the cells, incubations may be carried out at low temperature in the presence of the membrane and endosome marker FM 4-64. FM 4-64 is an effective marker for endocytosis because it specifically stains the endosomes involved in the endocytosis uptake. Observation of strong mixed signals (e.g., green from conjugated polymers or oligomers and red from FM 4-64) from both conjugated polymers or oligomers and FM 4-64 in the cell interior may be an indicator of internalization and the location of conjugated materials in the endosomes. This may provide direct evidence for the endocytosis uptake pathway. In another embodiment, incubation of the cells conjugated polymers or oligomers may be performed at two different temperatures, such as 4° C. and 37° C., in the presence of FM 4-64 to confirm the endocytosis pathway, wherein the endocytosis may be expected to work well at one temperature but not the other.

Additionally, one cell line may be incubated with a 460 nm emissive conjugated polymer or oligomer and another cell line may be incubated with a 530 nm emissive conjugated polymer or oligomer. Prior to co-culturing of the two different cell lines, we may mix these CPB-taking cell lines at the same population. Upon incubating for one hour, we may observe individual signals from the cells.

Example 20

Cell Imaging

General Procedure. After optimal conditions for cellular uptake of the conjugated polymer/oligomer have been determined, the cells may be grown on the surface of glass coverslips within microplate wells. The conjugated polymer/oligomer may then be added and allowed to interact with cell cultures, and the coverslips can be washed to remove excess nanoparticles. Coverslips may be carefully removed and prepared for confocal microscopy. Fluorescent confocal imaging methods may be employed to determine the extent of cellular uptake and to investigate localization of the conjugated polymer or oligomer within the cultured cells.

Example 21

Cell Imaging with Polymer 5

An aqueous solution of Polymer 5 (10 uL of 0.7 mg/ml in water) was transferred into a 96-well containing 3T3 L1-preadipocyte cells in culture media (100 uL). After 30-60 minutes of incubation at 37° C., the 96-well plate was placed on an inverted fluorescence microscope, and the cells were observed without washing using a DAPI band pass filter (Ex360/40, Em470/40).

Figure 10:
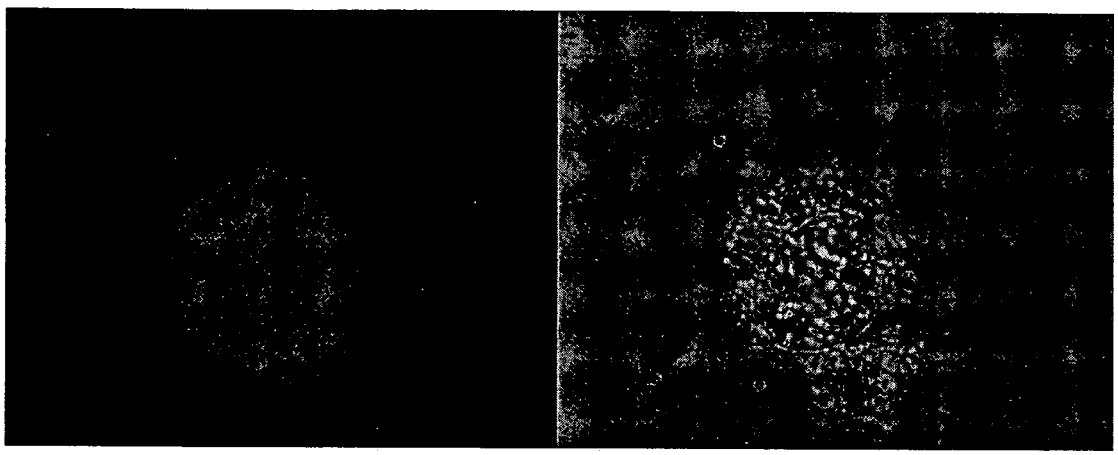
FIG. 10A shows the images produced from the fluorescence emission of a single cell that has internalized conjugated polymers of the invention (left image) and from the exposure of the cell to ambient light (right image) and FIG. 10B shows the images produced from the fluorescence emission of three aggregated cells that have internalized conjugated polymers of the invention (left image) and from the exposure of such cells to ambient light (right image).
Figure 10:
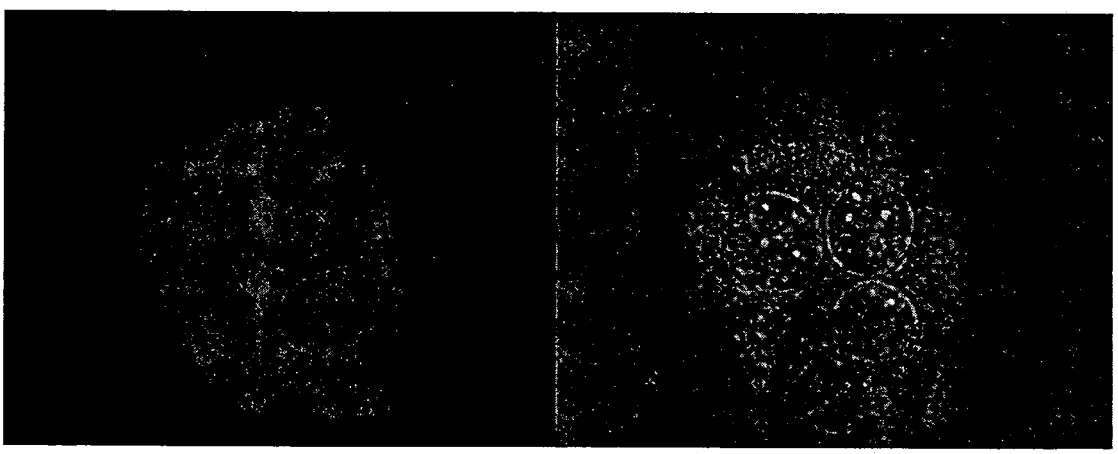
Figure 10:
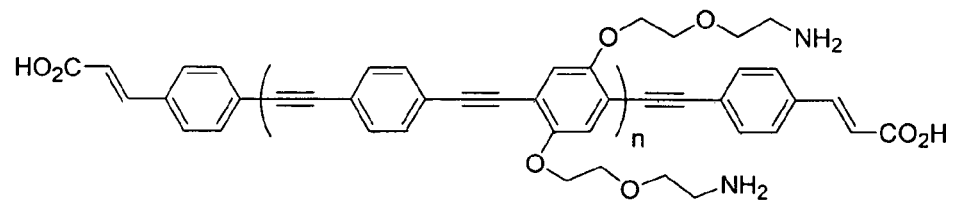

FIG. 10A shows a well containing a single cell, while FIG. 10B shows another well containing three cells aggregated together. In both examples, strong signals from the inside of the cells (cytosol and nucleola) were observed, with clear images of the nuclear membrane. The cells containing the conjugated polymers remained stable upon overnight incubation. The fluorescence emission of the polymer inside of the cell has sufficient intensity to suppress background signal and indicates efficient penetration of the cell by the conjugated polymer, even without washing away excess polymer that had not been internalized. Upon removal of any excess polymer, the intensity of the cell image may be expected to increase.

Definitions

The term "alkyl" may refer to saturated aliphatic groups, including straight-chain alkyl groups, branched-chain alkyl groups, cycloalkyl groups, alkyl-substituted cycloalkyl groups, and cycloalkyl substituted-alkyl groups.

The term "heteroalkyl" refers to an alkyl as described herein in which one or more carbon atoms is replaced by a heteroatom. Suitable heteroatoms include N, O, P, B, S, Si, Sb, Al, Sn, As, Se and Ge. In some preferred embodiments, the heteroatoms are O, N, or S. In one embodiment, the heteroalkyl group is poly(ethylene glycol).

The term "aryl" may refer to optionally substituted aromatic carbocyclic groups having a single ring (e.g., phenyl), multiple rings (e.g., biphenyl), or multiple condensed rings in which at least one is aromatic (e.g., naphthyl, anthryl, or phenanthryl).

"Heteroaryl" groups are aryl groups comprising at least one heteroatom as a ring atoms in an aromatic ring, with the remainder of the ring atoms being carbon atoms. Suitable heteroatoms include oxygen, sulfur, and nitrogen. Examples of heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted.

The term "aralkyl" refers to an alkylene group substituted with an aryl group. Suitable aralkyl groups may include benzyl, picolyl, and the like, and may be optionally substituted. "Heteroarylalkyl" refers to an alkylene group substituted with a heteroaryl group.

The terms "amine" and "amino" are recognized in the art and refer to both unsubstituted and substituted amines, e.g., a moiety that can be represented by the general formula: N(R')(R")(R'") wherein R', R", and R'" each independently represent a group permitted by the rules of valence.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted", as used herein, does not encompass replacement and/or alteration of a key functional group by which a molecule is identified, e.g., such that the "substituted" functional group becomes, through substitution, a different functional group. For example, a "substituted aldehyde" must still comprise the aldehyde moiety and can not be modified by substitution, in this definition, to become, e.g., a carboxylic acid. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, thiol, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, lower arylalkyloxyalkyl, and the like.

The term "carbonyl" is recognized in the art and refers to the group, C=O.

The term "carboxyl group" or "carbonyl group" is recognized in the art and can include such moieties as can be represented by the general formula:

wherein X is H, OH, O-alkyl, O-alkenyl, or a pharmaceutically acceptable salt thereof. Where X is O-alkyl, the formula represents an "ester". Where X is OH, the formula represents a "carboxylic acid". In general, where the oxygen atom of the above formula is replaced by sulfur, the formula represents a "thiolcarbonyl" group. Where X is a S-alkyl, the formula represents a "thiolester." Where X is SH, the formula represents a "thiolcarboxylic acid." On the other hand, where X is alkyl, the above formula represents a "ketone" group. Where X is hydrogen, the above formula represents an "aldehyde" group.

The term "acyl" refers to —C(O)R where R is alkyl, heterocycloalkyl, or aryl. The term "lower acyl" refers to where R is lower alkyl. The term $C_1$-$C_4$ acyl refers to where R is $C_1$-$C_4$. The term "acylamino" refers to —NHC(O)R where R is alkyl, heterocycloalkyl, or aryl. The term "acyloxy" refers to —OC(O)R where R is alkyl, heterocycloalkyl, or aryl. The term "sulfate" is given its ordinary meaning in the art and refers to the group, $SO_2$.

The term "sulfonate" is given its ordinary meaning in the art and refers to the group, $SO_3X$, where X may be an electron pair, hydrogen, alkyl, cycloalkyl, or aryl.

The term "carboxy esters" refers to —C(O)OR where R is alkyl, aryl, aralkyl, cyclic alkyl, or heterocycloalkyl, all optionally substituted.

The term "carboxyl" refers to —C(O)OH.

The terms "alkenyl" and "alkynyl" refer to unsaturated aliphatic groups analogous in length and possible substitution to the alkyls described above, but which contain at least one double or triple carbon-carbon bond, respectively. The term "alkenylalkyl" refers to an alkyl groups substituted with an alkenyl group. The term "alkynylalkyl" refers to an alkyl groups substituted with an alkynyl group.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl. "1-Alkenyl" refers to alkenyl groups where the double bond is between the first and second carbon atom. If the 1-alkenyl group is attached to another group, e.g. it is a W substituent attached to the cyclic phosphate, it is attached at the first carbon.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-Alkynyl" refers to alkynyl groups where the triple bond is between the first and second carbon atom. If the 1-alkynyl group is attached to another group, e.g. it is a W substituent attached to the cyclic phosphate, it is attached at the first carbon.

The term "alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched or cyclic. The alkylene may be optionally substituted with 1-3 substituents.

The term "alkoxy-" or "alkyloxy-" refers to the group alkyl-O—.

The term "electron-withdrawing group" or "electron-poor group" is recognized in the art and as used herein means a functionality which draws electrons to itself more than a hydrogen atom would at the same position. Exemplary electron-withdrawing groups include carbonyl groups (e.g., ketone, esters, aldehydes), sulfonyl, trifluoromethyl, nitro, cyano, and the like.

The term "electron-donating group" or "electron-rich group," as used herein, refers to a functionality which draws electrons to itself less than a hydrogen atom would at the same position. Exemplary electron-donating groups include amino, hydroxy, alkoxy, acylamino, acyloxy, alkyl, halide, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method of delivering a biological agent, comprising: introducing a polymer having a conjugated backbone and bound to a biological agent or an oligomer having a conjugated backbone and bound to a biological agent into a cell.

2. The method as in claim 1, wherein the polymer or the oligomer is emissive.

3. The method as in claim 1, further comprising substantially simultaneously monitoring light emission from the polymer or the oligomer in the cell, wherein the light emission indicates delivery of the biological agent into the cell.

4. The method of claim 1, wherein the polymer or oligomer is introduced into the cytoplasm.

5. The method of claim 1, wherein the polymer or oligomer is introduced into the nucleus.

6. The method of claim 1, further comprising exposing the polymer or the oligomer to a source of energy to cause an emission.

7. The method of claim 6, wherein the emission is fluorescence, phosphorescence, or chemiluminescence.

8. The method of claim 6, wherein the source of energy comprises electromagnetic radiation, electrical energy, sound energy, thermal energy, or chemical energy.

9. The method of claim 1, wherein the polymer or oligomer is soluble in aqueous solutions.

10. The method of claim 1, wherein the polymer or oligomer further comprises a biological recognition entity.

11. The method of claim 10, wherein the biological recognition entity is a peptide.

12. The method of claim 10, wherein the biological recognition entity is a nucleic acid.

13. The method of claim 10, wherein the biological recognition entity is a small interfering RNA (siRNA).

14. The method of claim 10, wherein the biological recognition entity is a carbohydrate.

15. The method of claim 10, wherein the biological recognition entity is an antibody.

16. The method of claim 1, wherein the polymer is a particle.

17. The method of claim 1, wherein the polymer is polyphenylene, polythiophene, polyaniline, polypyrrole, poly(phenylenevinylene), poly(phenyleneethylnylene), substituted derivatives thereof, or combinations thereof.

18. The method of claim 1, wherein the polymer or oligomer comprises a pendant group attached to the backbone.

19. The method of claim 18, wherein the pendant group comprises a charged group.

20. The method of claim 18, wherein the pendant group comprises an alkyl group, an alkoxy group, an aromatic group, a poly(ethylene glycol) group, a carbonyl group, a sulfate, an amine, an alcohol, a thiol, a cyanate, substituted derivatives thereof, or combinations thereof.

21. The method of claim 1, wherein the polymer or oligomer is associated with a biological agent.

* * * * *